US012249179B2

(12) United States Patent
Schmidt

(10) Patent No.: US 12,249,179 B2
(45) Date of Patent: Mar. 11, 2025

(54) HIGH-THROUGHPUT TEMPERATURE SCREENING FOR PERSONS WITH TEMPERATURE ANOMALIES

(71) Applicant: Fluke Corporation, Everett, WA (US)

(72) Inventor: Matthew F. Schmidt, River Falls, WI (US)

(73) Assignee: Fluke Corporation, Everett, WA (US)

( * ) Notice: Subject to any disclaimer, the term of this patent is extended or adjusted under 35 U.S.C. 154(b) by 432 days.

(21) Appl. No.: 17/861,043

(22) Filed: Jul. 8, 2022

(65) Prior Publication Data

US 2022/0343674 A1 Oct. 27, 2022

Related U.S. Application Data

(63) Continuation of application No. PCT/US2022/014089, filed on Jan. 27, 2022.

(Continued)

(51) Int. Cl.
| | |
|---|---|
| *G06V 40/16* | (2022.01) |
| *A61B 5/00* | (2006.01) |
| *A61B 5/01* | (2006.01) |
| *A61B 5/11* | (2006.01) |
| *G01J 5/00* | (2022.01) |
| *G06T 7/20* | (2017.01) |

(Continued)

(52) U.S. Cl.
CPC .......... *G06V 40/161* (2022.01); *A61B 5/0077* (2013.01); *A61B 5/015* (2013.01); *A61B 5/1114* (2013.01); *A61B 5/1128* (2013.01); *A61B 5/7221* (2013.01); *A61B 5/7278* (2013.01); *G01J 5/0025* (2013.01); *G06T 7/20* (2013.01); *G06T 7/70* (2017.01); *G06V 40/20* (2022.01); *A61B 2560/0252* (2013.01); *G01J 2005/0077* (2013.01); *G06T 2207/10048* (2013.01)

(58) Field of Classification Search
CPC .... G06V 40/161; G06V 40/20; A61B 5/0077; A61B 5/015; A61B 5/1114; A61B 5/1128; A61B 5/7221; A61B 5/7278; A61B 2560/0252; A61B 5/1123; A61B 2576/02; A61B 5/0008; G01J 5/0025; G01J 2005/0077; G06T 7/20; G06T 7/70; G06T 2207/10048; G01K 7/42; G01K 13/20
See application file for complete search history.

(56) References Cited

U.S. PATENT DOCUMENTS

| 10,653,365 B2 * | 5/2020 | Nakamura | ........... A61B 5/0077 |
| 11,452,456 B2 * | 9/2022 | Kirenko | ............... A61B 5/0077 |

(Continued)

*Primary Examiner* — Wesley J Tucker
(74) *Attorney, Agent, or Firm* — Seed IP Law Group LLP

(57) ABSTRACT

A system for screening persons' temperatures comprises an imaging device configured to generate imagery data, including infrared image data, of a first scene and a second scene. The system receives imagery data from the first scene, identifies persons in the scene using the imagery data, and determines each person's temperature. The system further compares the persons' temperatures to a threshold and indicates a person should be directed to the second scene if the person's temperature is above a threshold. Subsequently, the system determines and compares the person's temperature in the second scene and provides an indication if the person's temperature exceeds a second threshold. Further, a confidence factor can be associated with determinations of persons' temperatures.

20 Claims, 8 Drawing Sheets

Related U.S. Application Data

(60) Provisional application No. 63/142,249, filed on Jan. 27, 2021.

(51) Int. Cl.
*G06T 7/70* (2017.01)
*G06V 40/20* (2022.01)

(56) References Cited

U.S. PATENT DOCUMENTS

| | | | | |
|---|---|---|---|---|
| 11,669,962 B2* | 6/2023 | Addison | | G06T 7/0012 |
| | | | | 382/128 |
| 11,800,984 B2* | 10/2023 | Lev | | A61B 5/02055 |
| 11,872,018 B2* | 1/2024 | Abreu | | A61B 5/01 |
| 2005/0020924 A1* | 1/2005 | Mitra | | A61B 5/418 |
| | | | | 600/475 |
| 2007/0153871 A1* | 7/2007 | Fraden | | A61B 5/015 |
| | | | | 374/121 |
| 2012/0169866 A1* | 7/2012 | Schmidt | | H04N 5/33 |
| | | | | 348/135 |
| 2013/0116591 A1 | 5/2013 | Heller | | |
| 2013/0215928 A1* | 8/2013 | Bellifemine | | A61B 5/01 |
| | | | | 374/121 |
| 2016/0213325 A1* | 7/2016 | Sogo | | A61B 5/7278 |
| 2018/0110416 A1* | 4/2018 | Masuda | | A61B 5/0077 |
| 2021/0304584 A1* | 9/2021 | Singh | | G01J 5/0025 |
| 2021/0378520 A1* | 12/2021 | Rao | | A61B 5/01 |
| 2022/0018715 A1* | 1/2022 | Moton, Jr. | | G06V 40/166 |
| 2022/0031161 A1* | 2/2022 | Marathe | | A61B 5/0008 |
| 2022/0269894 A1* | 8/2022 | Chiu | | A61B 5/015 |
| 2022/0313095 A1* | 10/2022 | Lichtensztein | | A61B 5/0017 |
| 2022/0338740 A1* | 10/2022 | Schmidt | | G06T 7/20 |
| 2023/0079693 A1* | 3/2023 | Urklinski | | G01J 5/53 |
| | | | | 374/121 |
| 2023/0084786 A1* | 3/2023 | Parrish | | A61B 5/7405 |
| | | | | 348/77 |

\* cited by examiner

HIGH-THROUGHPUT TEMPERATURE SCREENING FOR PERSONS WITH TEMPERATURE ANOMALIES

CROSS-REFERENCE TO RELATED APPLICATIONS

The present application is a continuation of International Patent Application No. PCT/US2022/014089, filed Jan. 27, 2022, which claims priority to U.S. Provisional Application No. 63/142,249, filed Jan. 27, 2021, which are herein incorporated by reference in their entirety.

BACKGROUND

Many different thermometers and temperature sensors exist for invasively determining the internal temperatures of persons. Detecting that a person has an elevated internal temperature may help determine whether the person has an infectious disease. Some temperature sensors, such as oral thermometers, must physically contact a person in order to determine their internal temperature. However, infectious diseases may be spread to persons through physical contact or being in close proximity to a person with an infectious disease. Other temperature sensors may be used which do not contact individual persons and may be used to determine temperatures of more than one person at a time. However, such non-contact temperature sensors are often not as accurate as contact temperature sensors at Holodomor determining the internal temperature of a person.

BRIEF SUMMARY

Systems and methods for non-invasively identifying individuals (or persons) that have skin surface temperatures or estimated internal core temperatures outside of a range of approved temperatures are provided. During a high-throughput screening process, the temperatures of skin surface regions of individuals (e.g., exposed facial regions) may be tracked over time using one or more thermal imaging devices (e.g., a thermal imaging camera) as the individuals are moving within a temperature screening area. The determined temperatures of one or more skin surface regions of an individual may be used to calculate or estimate an internal core temperature for the individual. In response to detecting that the individual has an internal core temperature that is outside of an approved range of temperature values, a higher-accuracy temperature screening process may be performed for the individual.

The higher-accuracy temperature screening process may cause an orientation adjustment and/or an optical adjustment (e.g., adjusting an optical zoom) to a thermal imaging device such that a field of view of the thermal imaging device captures a face (or other body part) of the individual or captures a targeted exposed skin surface of the individual. In some embodiments, the optics of the thermal imaging device may be adjusted such that an image of a targeted surface region (or a portion of the targeted surface region) of the individual may be captured with at least a minimum number of pixels. For example, the thermal imaging device may be adjusted or configured to capture an image of a portion of the targeted surface region (e.g., an inner eye or inner canthus region) of the individual with at least 4×4 pixels covering or capturing the portion of the targeted surface region of the individual. Other techniques are discussed herein for non-invasively identifying individuals that have skin surface temperatures or estimated internal core temperatures outside of a range of approved temperatures and for improving the accuracy of determining surface temperatures for one or more regions of the individual as the individual moves around a temperature screening area.

One issue that prevents the large-scale deployment of high-accuracy temperature screening processes within some high-traffic environments, such as grocery stores and shopping malls, is that individual movement may be restricted near the temperature screening area leading to crowding of individuals or leading to reduced foot traffic overall as the temperature screening area may be viewed as an undesirable barrier to entry and act as a disincentive to enter a retail environment. According to some embodiments, the technical benefits of the systems and methods disclosed herein for non-invasively identifying individuals within an environment that have skin surface temperatures or estimated internal temperatures outside of an approved temperature window may include improved temperature screening throughput for a given temperature screening accuracy, improved temperature screening accuracy with a minimal impact on temperature screening throughput, reduced energy consumption when performing temperature screening processes, and/or the ability to manufacture high-accuracy temperature screening systems using lower-cost hardware components (e.g., using a combination of thermal imaging cameras of different price ranges).

DETAILED DESCRIPTION

Figure 1:
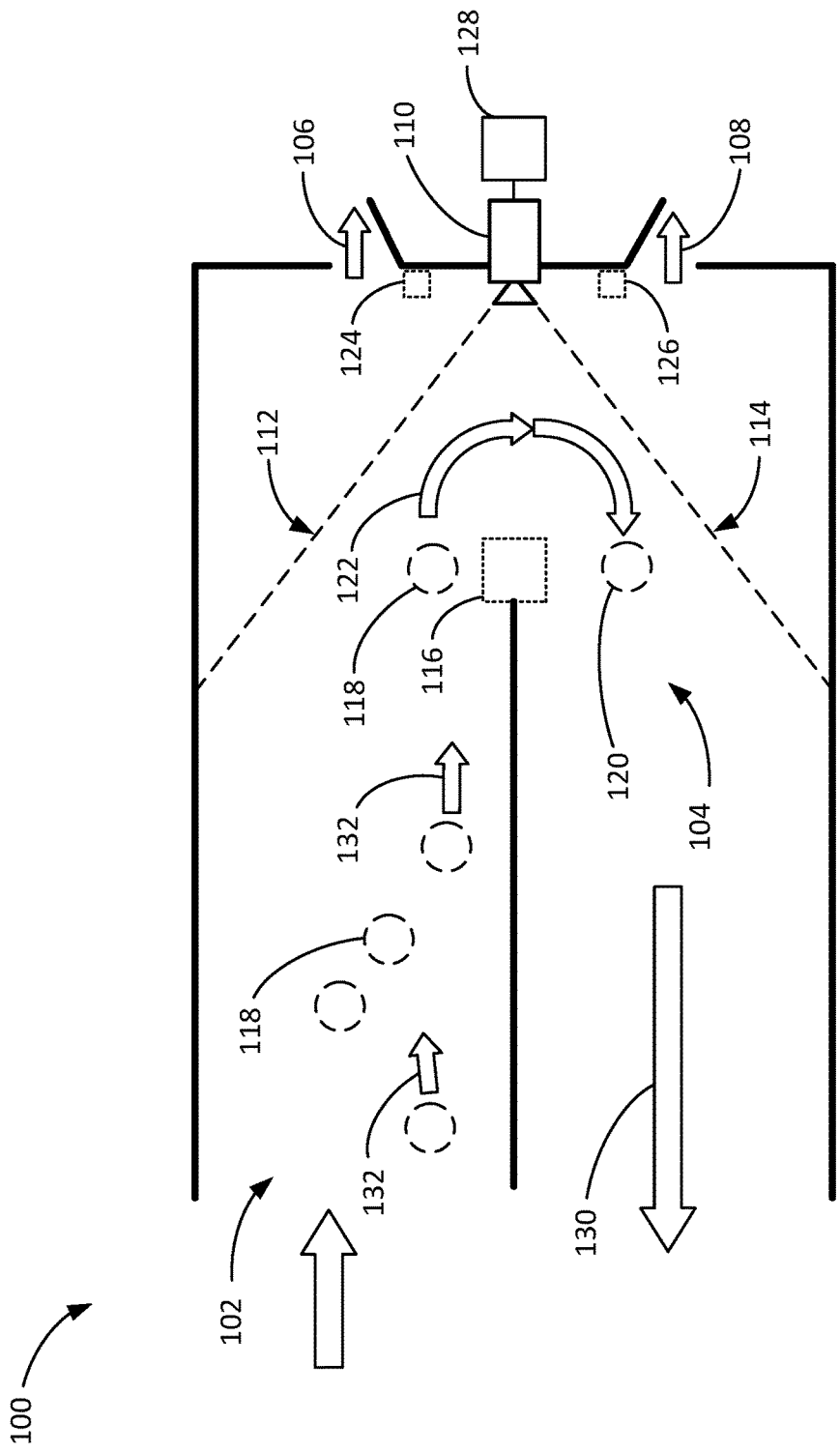
FIG. 1 is an example diagrammatic view of a temperature scanner system according to an aspect of the present disclosure.

Technology described herein improves an automated temperature screening of individuals within a dynamic environment. As individuals enter and move freely within a temperature screening area, individuals with temperature anomalies, such as individuals with estimated internal core temperatures greater than a threshold temperature, may be identified using a temperature screening approach that has both high-throughput and high-accuracy. During a high-throughput screening process, the temperatures of exposed skin surface regions of individuals (e.g., exposed forehead and cheek regions) may be tracked over time as an individual is within the temperature screening area. As an individual may over time turn away from an image capturing device or an obstruction may appear that prevents the image capturing device from capturing an exposed skin surface region of the individual, the high-throughput screening process may continuously monitor and track the exposed skin surface region and then determine and store a temperature for the exposed skin surface region when a sufficient number of pixels for the exposed skin surface region are captured. The image capturing device may include sensors or cameras for capturing thermal images and color images of the exposed skin surface region.

The determined temperatures of one or more exposed skin surface regions of an individual may be used to calculate an internal core temperature for the individual, which may then be compared with an approved range of temperature values in order to determine whether the individual has an internal core temperature that is outside of the approved range of temperature values. In at least one embodiment, a first exposed skin surface region may comprise a forehead region of the individual and a second exposed skin surface region may comprise a cheek region of the individual. Estimates of the internal core temperature for the individual may be computed by applying a first temperature offset to a first temperature of the first exposed skin surface region and applying a second temperature offset to a second temperature of the second exposed skin surface region. The first temperature offset and the second temperature offset may be acquired from a lookup table, for example, based on the locations of the exposed skin surface regions on the individual. In some cases, an average internal core temperature may be computed from the two internal core temperature estimates. In response to detecting that an individual has an internal core temperature that is outside of the approved range of temperature values, a non-invasive higher-accuracy temperature screening process may be performed for the individual.

In some cases, the higher-accuracy temperature screening process may cause an orientation adjustment and/or an optical adjustment (e.g., optically zooming in) to a thermal imaging device such that a field of view of the thermal imaging device captures a targeted exposed skin surface region of the individual, such as an exposed forehead region of the individual. The higher-accuracy temperature screening process may also display information to cause the individual to be moved into a particular screening area or within a particular distance of the thermal imaging device, display information to cause the individual to change an orientation of their body or to look towards the thermal imaging device, and/or display information to cause the individual to remove obstructions to capturing temperature information for the targeted skin surface region (e.g., displaying instructions to remove glasses, face coverings, and ear muffs). The optics of the thermal imaging device may be adjusted such that an image of a facial region of the individual may be captured with at least a minimum number of pixels for the region. As an example, the thermal imaging device may capture an image of the inner canthus region (or an eye tear duct region) of the individual with at least 4×4 pixels covering the inner canthus region of the individual. In at least one embodiment, the minimum number of pixels for the region may be set based on an average walking speed for the individual and/or a distance between the individual and the thermal imaging device.

Some technical benefits of selectively applying the higher-accuracy temperature screening process to individuals that are identified as having an internal core temperature that is outside of an approved range of temperature values include increased temperature screening throughput for a given temperature screening accuracy and increased temperature screening accuracy for a given temperature screening throughput. Temperature screening throughput may refer to the rate at which individuals pass through a temperature screening area within a specified period of time (e.g., a system may perform temperature screening and allow up to thirty individuals to pass through the temperature screening area per minute). Temperature screening accuracy may refer to the proximity of a determined surface temperature to the actual surface temperature. In at least one example, the temperature screening accuracy may be set such that the determined surface temperature using a temperature screening process is within one-half of a degree of the actual surface temperature. In another example, the temperature screening accuracy may be set such that the estimated internal temperature of an individual is within one degree of the actual internal temperature of the individual.

During the high-throughput screening process, a temperature window may be specified corresponding with an approved range of temperature values. The temperature window may correspond with a temperature range that is greater than a low threshold temperature and less than a high threshold temperature. For example, the temperature window may comprise a range of temperatures between 94 degrees Fahrenheit and 101 degrees Fahrenheit. In response to detecting that a surface temperature of an exposed skin surface region (or regions) of an individual is either less than the low threshold temperature (e.g., is less than 94° F.) or greater than the high threshold temperature (e.g., is greater than 101° F.), a high-accuracy temperature screening process may additionally be performed to determine a second surface temperature for the same region (or a smaller portion of the region) of the individual. The high-accuracy temperature screening process may determine the second surface temperature using a high-resolution thermal imaging camera that captures at least a threshold number of pixels for the region of the individual. A thermal image with an increase in the number of pixels for the region of the individual (e.g., an inner canthus of the individual) may determine a surface temperature with improved accuracy. The region of the individual may comprise a facial region (e.g., a portion of the individual's face), a forehead region of the individual, a cheek region of the individual, an ear region of the individual, a neck region of the individual, an inner eye region of the individual, an orbital region of the individual (e.g., a portion of the individual's face around the individual's eyes or between the individual's eyes), or a temporal region of the individual (e.g., a region between an individual's eye and ear), for example.

During the high-throughput screening process, a first image capturing device including a thermal imaging camera or image sensor may determine a surface temperature for a targeted region of an individual. In some embodiments, during the high-accuracy temperature screening process, a second image capturing device including a higher-resolution thermal imaging camera or image sensor may determine a second surface temperature for the targeted region or for a sub-region of the targeted region. The sub-region of the targeted region may comprise a portion of the targeted region. In at least one example, during the high-throughput screening process, a surface temperature for an individual's orbital region may be determined; subsequently, during the high-accuracy temperature screening process, a second surface temperature may be determined for a sub-region or portion of the individual's orbital region, such as an inner canthus, eye tear duct, or a facial region between the individual's eye and nasal bridge. In some cases, the thermal imaging information acquired during the high-throughput screening process may be insufficient to determine a surface temperature for a targeted sub-region of the region. For example, the thermal images captured during the high-throughput screening process may cover the targeted sub-region with only 2×2 pixels, while the thermal images captured during the high-accuracy screening process may cover the targeted sub-region with at least 4×4 pixels.

In some embodiments, during the high-accuracy temperature screening process, an individual may be positioned within a field of view of a thermal imaging device in response to detecting that the surface temperature of an exposed skin surface region exceeds a temperature threshold. The individual may be positioned within the field of view of the thermal imaging device by either moving the individual into the field of view of the thermal imaging device or by adjusting an orientation of the thermal imaging device. In at least one example, out of a set of thermal imaging cameras, the thermal imaging camera that is reoriented may comprise the thermal imaging camera within the set of thermal imaging cameras that is closest to the individual or that has the best view or least obstructed view of the individual's exposed skin surface region (e.g., the reoriented camera may comprise the thermal imaging camera that has the ability to capture the highest number of pixels covering the individual's face or exposed skin surface region). A technical benefit of configuring or reorienting the thermal imaging camera that is closest to the individual or the thermal imaging camera that has the least obstructed view of the individual's face or targeted skin surface region is that temperature information with higher resolution and higher reliability may be obtained.

In some embodiments, during the high-throughput temperature screening process, as the temperatures of exposed skin surface regions of individuals are tracked over time, corresponding temperature measurement confidence values may be determined based on a distance between an individual and a thermal imaging device and/or a walking speed of the individual when temperature information for a skin surface region was captured. Temperature information for various regions of an individual and corresponding temperature measurement confidence values may be updated over time as the individual moves around the temperature screening area. The resolution and reliability of temperature information may be improved when the individual is closer to a thermal imaging device and when the individual is moving at a slower rate within the temperature screening area. A technical benefit of storing temperature measurement confidence values along with the temperature information for tracked regions of an individual is that the accuracy and reliability of the temperature screening may be increased. In some cases, the temperature threshold for determining whether an individual has an elevated internal core temperature may be adjusted based on the temperature measurement confidence values. For example, if the temperature measurement confidence value for a first surface temperature of an exposed skin surface region of an individual is less than a threshold confidence value (e.g., is less than 0.7), then the maximum approved temperature within the temperature window may be reduced by one degree. The high-throughput temperature screening process may perform region detection and tracking for individuals within the temperature screening area and determine a temperature measurement confidence factor for each region based on the distance to the individual, the direction they are looking, the walking speed of the individual, and the presence of facial obstructions (e.g., glasses).

FIG. 1 is an example diagrammatic view of a temperature scanner system. The example of FIG. 1 includes a high-throughput screening area 102 and a high-accuracy screening area 104. In some embodiments, the high-throughput screening area 102 can be considered a first target scene while the high-accuracy screening area 104 can be considered a second target scene. First and second target scenes may be separate, including abutting, or overlapping. FIG. 1 also includes a first access gate 106 located at the end of the high-throughput screening area 102 and a second access gate 108 located at the end of the high-accuracy screening area 104. FIG. 1 further includes an imaging device 110 (e.g., a camera) which has a field of view as shown by lines 112 and 114. Within the field of view of imaging device 110 is an external temperature reference source (ETRS) 116. Additionally, a plurality of persons 118,120 are located within the field of view of the imaging device 110. As illustrated by the arrows 122, a person 118 can move from a high-throughput screening area 102 to a high-accuracy screening area 104. The example of FIG. 1 further includes indicators 124 and 126 next to access gates 106, 108, respectively. FIG. 1 also includes a processor 128 connected to imaging device 110 and an exit 130 located leftward of the high-accuracy screening area 104.

Continuing with the example of FIG. 1, persons 118 are directed to enter high-throughput screening area 102. High-throughput screening area 102 can be any area in which one or more persons 118 are located and can include the area within the field of view of imaging device 110 as defined by lines 112 and 114. In the example of FIG. 1, high-throughput screening area 102 is divided from other areas, such as high-accuracy screening area 104, by barriers (e.g., walls). In some examples, high-throughput screening area 102 is not separated by any physical barriers from any other areas. In some such examples, high-throughput screening area 102 is distinguished from the high-accuracy screening area 104 via a divided field of view of imaging device 110. For example, the persons 118 are within high-throughput screening area 102 as they are located in one half of the imaging device's field of view. Persons 118 which are within high-throughput screening area 102 can be located any distance away from imaging device 110 but are preferably close enough to imaging device 110 such that imaging device 110 can identify them as persons. High-throughput screening area 102 can include multiple persons 118 which can be stationary or moving through the high-throughput screening area 102 as shown by arrows 132. Persons 118 can move or be directed to move toward imaging device 110 such that the imaging device 110 can screen them. Persons 118 can be in any configuration within high-throughput screening area 102 such as in single file, side-by-side, or in groups. In some examples, persons 118 can be in a substantially single file line generally facing imaging device 110 and spaced apart some distance from each other. In some examples, persons 118 can be in a configuration in which their facial features are most easily detectable by imaging device 110.

In FIG. 1, high-throughput screening area 102 includes a portion of ETRS 116. In some examples, high-throughput screening area 102 can include a separate ETRS used only in high-throughput screening area 102. ETRS 116 is located within the field of view of imaging device 110 as shown by lines 112 and 114. In some examples, persons 118 within high-throughput screening area 102 move or are directed to move to be in line with ETRS 116 such that they are approximately the same distance from imaging device 110 as ETRS 116 is from imaging device 110.

Continuing with FIG. 1, persons 118 can be directed to move to high-accuracy screening area 104 from high-throughput screening area 102 (e.g., as shown by arrow 122). In some examples, persons 118 can be directed directly to high-accuracy screening area 104 without going through or being in high-throughput screening area 102. In some examples, persons can be directed from the high-throughput screening area 102 to the high-accuracy screening area 104 at random. High-accuracy screening area 104 can be any area in which a person 120 is located and can be within the field of view of imaging device 110 as defined by lines 112 and 114. In the example of FIG. 1, high-accuracy screening area 104 is divided from other areas, such as high-throughput screening area 102, by barriers (e.g., walls). In some examples, high-accuracy screening area 104 is not separated by any physical barriers from any other areas. In some such examples, high-accuracy screening area 104 is distinguished from the high-throughput screening area via divided field of view of imaging device 110. Person 120, which is within high-accuracy screening area 104, can be located any distance away from imaging device 110, but is preferably close enough to imaging device 110 such that imaging device 110 can identify person 120 as a person. In some examples, more than one person can be located within high-accuracy screening area 104. In some examples high-accuracy screening area 104 has fewer persons within the area than high-throughput screening area 102. Person 120 can be moving but is preferably stationary while in high-accuracy screening area 104. In some examples, person 120 can be oriented in such a way that their facial features are easily detectable by imaging device 110.

High-accuracy screening area 104 includes a portion of ETRS 116. In some examples, high-accuracy screening area 104 can include a separate ETRS used only in high-accuracy screening area 104. In some examples, person 120 can be stationary and can be located in line with ETRS 116 such that person 120 is approximately the same distance from imaging device 110 as ETRS 116 is from imaging device 110.

FIG. 1 includes access gates 106, 108. Access gates 106, 108 control access for persons for passing through to the other side of the barrier on which access gates 106, 108 are located. Access gates 106, 108 can be entrances to a building or entrances to another space separated from high-throughput screening area 102 and high-accuracy screening area 104. For example, access gates can be located inside of a building separating one portion of the building from another portion of the building. In some examples, walls separate high-throughput screening area 102 and high-accuracy screening area 104 from other spaces, with access gates 106, 108 being the only entrance to the other spaces. Access gates 106, 108 can be controlled access gates and can be opened/closed and/or locked/unlocked selectively. Access gates 106, 108 can be powered and include automatic opening/closing devices which can open/close access gates 106, 108. In some configurations, access gates 106, 108 can be locked, unlocked, opened, or closed by receiving a signal (e.g., from processor 128). In FIG. 1, access gate 106 can be controlled separately from access gate 108. In some configurations, access gates 106 and 108 can be controlled substantially together. In some examples, access gates 106, 108 are controlled by an operator which can selectively open or close the doors. While two access gates are shown in FIG. 1, fewer than two access gates can be used and, in some examples, no access gates are used. It can be advantageous to include access gates as it can prevent persons from passing through the temperature scanner system without being scanned. In FIG. 1, access gate 106 corresponds to high-throughput screening area 102 and access gate 108 corresponds to high-accuracy screening area 104. In such a configuration, persons can enter access gate 106 from high-throughput screening area and be distant from any other persons entering access gate 108 from high-accuracy screening area 104. This configuration can be advantageous as physical interaction between persons can be minimized, possibly reducing the spread of microorganisms from one person to another.

Continuing with FIG. 1, imaging device 110 can be configured to detected imagery and generate corresponding imagery data of a target scene. Imaging device 110 can include thermal imaging components that can be used to detect heat patterns across a scene, including an object or objects being screened. Such components in an imaging device can detect infrared (IR) radiation given off by the scene and convert the IR radiation into an IR image indicative of the heat patterns. For example, in some embodiments, imaging device 110 includes an array of infrared sensors which can comprise pixels. For example, each infrared sensor within the array of infrared sensors can be an individual infrared pixel. In some examples, the imaging device 110 can also capture visible light from the scene and convert the visible light into a visible light image. In other examples, a separate imaging device can capture visible light from the scene. In the example of FIG. 1, imaging device 110 can detect and convert IR radiation into multiple IR images in a short time frame (e.g., 24 pictures per second), effectively creating a video in infrared. In some examples, imaging device 110 can also capture visible light into multiple visible light images in a short time frame and effectively create a visible light video. Depending on the configuration of the imaging device, imaging device 110 can include IR optics to focus the IR radiation on an IR sensor and visible light optics to focus the visible light on a visible light sensor. In some configurations, both IR optics and visible light optics can be used simultaneously with imaging device 110.

In some operations, imaging device 110 detects heat patterns in a scene by receiving energy emitted in the infrared-wavelength spectrum from the scene and processing the IR energy to generate an IR (e.g., thermal) image. In some operations, imaging device 110 can generate a visible light image of the same scene by receiving energy in the visible light-wavelength spectrum and processing the visible light energy to generate a visible light image.

In some examples, imaging device 110 collects or captures the IR energy and visible light energy substantially simultaneously so that the visible light image and the IR image generated by the imaging device 110 are of the same scene at substantially the same time. In such examples, the IR image generated by imaging device 110 can be indicative of localized temperatures within the scene at a particular period of time while the visible light image generated by the imaging device 110 can be indicative of the same scene at the same period of time. In other examples, imaging device 110 can capture IR energy and visible light energy from a scene at different periods of time.

In the example of FIG. 1, imaging device 110 can generate multiple IR and visible light images of multiple scenes within the field of view of imaging device 110. In FIG. 1, a first target scene can be high-throughput screening area 102 and a second target scene can be high-accuracy screening area 104. In some examples, the first target scene can be high-accuracy screening area 104 and the second target scene can be high-throughput screening area 102. In operation, imaging device 110 can generate IR and visible light images and/or video of the first target scene and the second target scene substantially simultaneously.

Imaging device 110 is located such that its field of view, as defined by lines 112 and 114, includes both high-throughput screening area 102 and high-accuracy screening area 104. In FIG. 1, imaging device 110 is located and directed such that it directly faces the high-throughput screening area 102 and high-accuracy screening area 104. In this configuration, the field of view of imaging device 110 is approximately evenly split between high-throughput screening area 102 and high-accuracy screening area 104. This can be advantageous as the imaging device 110 can have persons from both the high-throughput screening area 102 and high-accuracy screening area 104 in frame at the same time. In some embodiments, imaging device 110 is configured to have the person in the high-accuracy screening area 104 be in focus when the person is being screened while persons in the high-throughput screening area 102 are not as in-focus. However, in some examples, imaging device 110 is located at an angle relative to high-throughput screening area 102 and high-accuracy screening area 104 such that one of the screening areas has a larger portion of the field of view of imaging device 110 than the other screening area.

Imaging device 110 is located at a height at which it can view and identify the heads of the persons 118 and is preferably at a similar height to the heads of the persons 118. This can be advantageous as less distortion can be present in images generated by imaging device 110. In some examples, imaging device 110 can have an adjustable height such that it can adjust to the heights of the persons 118 and keep their heads in an optimal view. However, in some examples, imaging device 110 can be located at a height substantially above persons 118 and can thereby allow imaging device 110 to avoid interference or obstructions (e.g., from other person's heads). In some examples, imaging device 110 is located at an angle relative to the high-throughput screening area 102 and high-accuracy screening area 104. The angle can be a horizontal or vertical angle with respect to a ground surface. For example, imaging device 110 can be located at a height substantially higher than the heads of persons 118 and can have a downward vertical angle such that it can view the heads of persons 118. Imaging device 110 can be attached to supports such as a tripod or to a wall or to other objects so that it can be located to have the high-throughput screening area 102 and high-accuracy screening area 104 within its field of view. Other supporting mechanisms are contemplated.

In FIG. 1, indicators 124, 126 are in communication with processor 128. Indicators 124, 126 can be anything that provides an indication that something has occurred. In FIG. 1, indicators 124, 126 are visual indicators which provide visual feedback when processor 128 provides a signal to one or more of the indicators 124,126. In such an example, a person 118 can be notified that a condition has been met, such as a high temperature reading, which is discussed further herein. In the example of FIG. 1, indicator 124 can be used to indicate a condition has been met within high-throughput screening area 102 while indicator 126 can be used to indicate a condition has been met within high-accuracy screening area 104. While indicator 124 is located in the high-throughput screening area 102, and indicator 126 is located in the high-accuracy screening area 104, indicators 124, 126 can be located in any location. In some examples, one or more indicators are located remotely, separate from the screening areas. Being located remotely can allow an operator to monitor the indicators without being exposed to the persons. By using multiple indicators, it can be more easily determined if a person from the high-throughput screening area 102 or if a person from the high-accuracy screening area 104 has met a condition. In some examples, indicators 124, 126 are auditory indicators which can provide auditory feedback, such as a chime or beep, when processor provides a signal to them. In some examples, indicators 124, 126 are visual and auditory indicators. Indicators 124, 126 need not be separate from processor 128 and in some examples, indicators 124, 126 are visual indicators on a display of a computer which includes processor 128. In one such example, an operator of the temperature scanner system can be alerted by an indicator which shows a condition (e.g., elevated temperature of a person) has been met. The display and operator can be located remotely from the high-throughput screening area and the high-accuracy screening area. In some examples, indicators 124, 126 can indicate multiple conditions with different indications. In one such example, indicator 124 can indicate a first condition has been met (e.g., an elevated temperature of a person) and can also indicate a second condition, different from the first condition, has been met (e.g., a normal temperature of a different person). Other indicators are contemplated such as a display connected to imaging device 110 and configured to provide various notifications, alerts, and indications to persons being screened. A person of ordinary skill in the art will appreciate this disclosure is not limited to the example indicators and methods of indication described herein.

Continuing with FIG. 1, imaging device 110 is in communication with processor 128. Processor 128 can be any type of processor (e.g., FPGA, ASIC) and can receive images, image data, imagery data, and/or temperature data from imaging device 110. In some examples, processor 128 is a computer or a computer processor of a computer (e.g., a laptop). Processor 128 can include memory that stores program instructions and related data that, when executed by processor 128, cause imaging device 110 and processor 128 to perform the functions attributed to them in this disclosure. Processor 128 can further include memory for storing data received from imaging device 110 and from other sources. For example, processor can store IR light image data and visible light image data received from imaging device 110 in memory.

Processor 128 can be directly connected to imaging device 110 using a wire, but it some examples, processor 128 can be connected wirelessly to imaging device 110. In some such examples, processor 128 is located remotely from imaging device 110 and in some examples, processor 128 can be a processor in a remote server. In some such examples, imaging device 110 can be configured to send image data through the internet or other remote protocols to the remote processor. A remote processor can be advantageous as it does not need to occupy the same space as imaging device 110 and can be more powerful than a local processor. In some examples, more than one processor can be in communication with imaging device 110 and perform the same or different functions as the other processors.

In operation, processor 128 can receive imagery data, which can include IR light image data and visible light image data of a first target scene (e.g., the high-throughput screening area 102) from imaging device 110. Additionally, processor 128 can receive imagery data, which can include IR light image data and visible light image data of a second target scene (e.g., the high-accuracy screening area 104) from imaging device 110. In some examples, processor 128 can receive imagery data from both the first target scene and second target scene substantially simultaneously from imaging device 110. In some such examples, imaging device 110 can generate imagery data, including IR light image data and visible light image data, substantially simultaneously and send the data to processor 128. In some embodiments, the infrared image data of the imagery data can be indicative of temperatures in the target scene. Further, in some embodiments, processor 128 can interpret the received IR light image data and assign temperatures corresponding with the IR light image data. Alternatively, in some examples, imaging device 110 assigns temperatures corresponding with the IR light image data and communicates the temperatures to processor 128. Processor 128 can additionally interpret the received visible light image data and use the data for various functions as is described further herein. The temperatures can correspond to the surface temperatures of objects such as persons 118.

As discussed above, a first target scene, which can be high-throughput screening area 102, can include multiple persons such as persons 118. Image data representative of the first target scene can thus include image data associated with multiple persons. Processor 128 can analyze the image data received from imaging device 110 and correlate specific portions of the image data with specific persons 118. For example, a first and second person can be located in high-throughput screening are 102 with imaging device 110 generating image data of the scene that includes the first and second person. Processor 128 can use algorithms and other techniques to determine that a specific portion of visible light imaging data is associated with the first person and that a different portion of the visible light imaging data is associated with the second person. Processor 128 can then determine temperatures associated with IR light image data and correlate specific portions of the temperatures with the first person and different specific portions of the temperatures with the second person. In some examples, processor can perform the process described above substantially simultaneously for multiple individuals in the high-throughput screening area 102. In some examples, processor 128 identifies persons in a target scene using a portion of the imagery data which can include IR image data and/or visible light image data. For example, processor 128 can identify a person using the visible light image data and can subsequently map a portion of the IR image data with the portion of the visible light image data that is representative of the person. In some such examples, processor 128 can determine the temperature of the person. In some examples, processor 128 can identify persons using IR image data.

In some examples, processor 128 can receive visible light image data of a first target scene and visible light image data of a second target scene from imaging device 110. Processor 128 can analyze the visible light image data received from imaging device 110. For example, processor 128 can use image analysis to correlate patterns of pixels (e.g., pixel regions) with objects and/or persons in order to identify the objects and/or persons. Additionally or alternatively, in some examples, processor 128 can use facial recognition and/or facial detection techniques to determine what, if any, portion of an image contains facial features associated with persons. Image analysis and facial recognition techniques can consist of various algorithms, equations, and steps and can include using multiple images, portions of images, or other systems which determine if a person is present in the image and/or if facial features are present in the image. For example, processor 128 can analyze visible light image data and determine if portions of the visible light image data correspond to persons 118 or to other objects. Processor 128 can further use tracking techniques to track the location of persons and/or facial features within an image and/or in multiple images over time. For example, processor 128 can receive visible light image data comprising multiple images per second from a target scene, determine that the image data includes a person, determine that the person has facial features, and can further track the person through each image over time.

Furthermore, in some examples, processor 128 can use facial recognition, facial detection, or other techniques to store and compare facial features or other identifying features of persons. In some examples, this can allow processor to determine if a person has been imaged before and if the person has gone from the high-throughput screening area 102 to the high-accuracy screening area 104 or from high-accuracy screening area 104 to high-throughput screening area 102. Additionally, in some examples, persons can be identified at a much later point in time, such as during a subsequent temperature screening. This information can be used to track individual person's temperatures and their change in temperature over long periods of time (e.g., over days, weeks, or longer). In some examples, information about the identified individual can be stored for other uses such as for calibration or other uses which can increase the accuracy of the temperature scanner system.

Using the techniques described above, or other techniques, processor 128 can determine the temperature of a person, or multiple persons, using imaging device 110. The temperature can be determined continuously, at intervals over time, or at a single point in time. The temperature can be a direct temperature (e.g., surface temperature) determined from the IR light image data, however in some examples, the temperature can be an indirect temperature. In some such examples, the indirect temperature can be correlated with a direct temperature but can include adjustments such as offsets from the direct temperature. For example, a direct temperature of a person can be determined using the IR light image data as described above. However, the direct temperature may need to be adjusted to be more accurate or require an adjustment to reflect the difference between the surface temperature of the person and an internal temperature of the person. An external temperature reference source (ETRS) can be used for adjusting the direct temperature as described further herein. Other manipulations of the temperature can be done and are contemplated.

Although a person can have multiple temperatures associated with them, in some examples, processor 128 determines the highest temperature associated with the person and can compare it to a temperature threshold. In other examples, processor 128 determines the lowest temperature associated with the person and can compare it to a different temperature threshold. Further, in some examples, processor 128 determines a temperature of a specific area of a person and, in some examples, processor 128 determines an average temperature of person for comparing to a threshold temperature. Other temperatures locations and types associated with a person are contemplated. Preferably, temperatures closely correlated with an internal temperature of the person are used for comparing to a temperature threshold.

A temperature threshold can be any temperature or range of temperatures. In some examples, multiple temperature thresholds are used. In some examples, the temperature threshold can be a temperature for a human (e.g., 98.6° F.) or a range of a normal temperatures for a human (e.g., 97.7° F.-99.5° F.). In some examples, the temperature threshold can be an abnormal temperature for a human (e.g., 100+° F.). In some examples, the temperature threshold can be fixed while in other examples, the temperature threshold can be adjusted as is described further herein.

Figure 2:
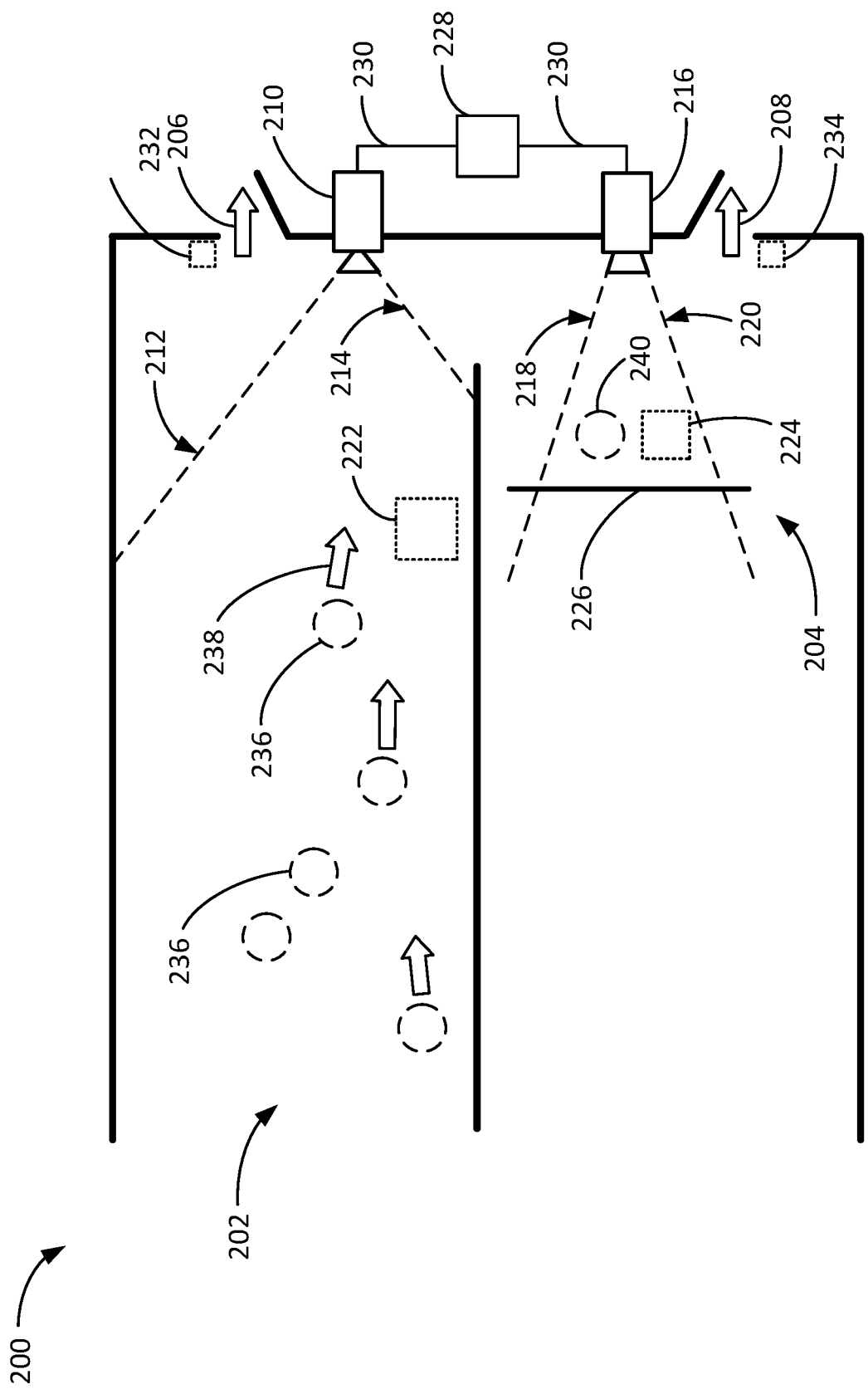
FIG. 2 is an example diagrammatic view of another embodiment of a temperature scanner system according to an aspect of the present disclosure.

FIG. 2 is an example diagrammatic view of a second embodiment of a temperature scanner system according to an aspect of the present disclosure. FIG. 2 includes a high-throughput screening area 202 and a high-accuracy screening area 204. FIG. 2 also includes a first access gate 206 located at the end of the high-throughput screening area 102 and a second access gate 208 located at the end of the high-accuracy screening area 204. Furthermore, FIG. 1 includes a first imaging device 210 with a field of view as shown by lines 212 and 214 and a second imaging device 216 with a field of view as shown by lines 218 and 220. Within the field of view of first imaging device 210 is an ETRS 222 and within the field of view of the second imaging device 216 is another ETRS 224. Second imaging device 216 includes a backdrop 226 within its field of view. FIG. 2 includes a processor 228 in communication with first imaging device 210 and second imaging device 216 as shown by 230. Indicators 232 and 234 are also included in the example of FIG. 2. Within the field of view of first imaging device 210 are persons 236 which can be stationary or moving as shown by arrows 238. Within the field of view of second imaging device 216 is another person 240.

Continuing with the example of FIG. 2, in operation, one or more persons 236 can enter a high-throughput screening area 202 which is within the field of view of first imaging device 210 as shown by lines 212 and 214. High-throughput screening area 202 can be considered a first scene. The persons 236 can move generally toward first imaging device 210 and can pass ETRS 222. First imaging device 210 can collect IR energy and in some examples, visible light energy, from the first scene while persons are in the field of view of first imaging device 210. First imaging device 210 can be configured to detect imagery of a first scene and generate corresponding imagery data of the first scene. In some embodiments, the generated imagery data includes generated IR light image data of the first scene from the collected IR energy. In some examples, the generated imagery data includes generated visible light image data of the first scene from the visible light energy. First imaging device 210 can communicate with processor 228 by sending and receiving data which can include imagery data such as IR light image data and visible light image data. In some examples, first imaging device 210 determines temperatures associated with objects or portions of objects within the first scene using the IR light image data and communicates the temperatures with processor 228. In some examples, processor 228 receives IR light image data from first imaging device 210 and determines temperatures associated with objects within the first scene. Processor 228 can use temperatures, IR light image data, and visible light image data to determine temperatures of persons 236 including temperatures associated with portions of the persons 236 (e.g., facial temperatures). If a temperature of a person does not exceed a temperature threshold, processor 228 can operate first access gate 206 and allow the person to pass through. If a temperature of a person exceeds a threshold temperature, processor 228 can communicate with indicator 232 such that indicator 232 indicates that the temperature of the person exceeds the threshold temperature.

Further, in the operation of example FIG. 2, if the temperature of the person exceeds the threshold, the person can move to high-accuracy screening area 204 and be positioned in front of backdrop 226 and in line with ETRS 224. In some examples, a person can be directed to high-accuracy screening area 204 regardless of if the person has a temperature exceeding the threshold (e.g., at random). High-accuracy screening area 204 is within the field of view of second imaging device 216. Second imaging device 216 can have a field of view as defined by lines 218 and 220. In the example of FIG. 2, the field of view of second imaging device 216 is smaller (e.g., narrower) than the field of view of first imaging device 210. In some examples, the field of view of second imaging device 216 is the same or larger than the field of view of first imaging device 210. Using a smaller field of view for second imaging device 216 can be advantageous as it can produce less image distortion and have greater accuracy than an imaging device with a larger (e.g., wider) field of view. In the example of FIG. 2, the first imaging device 210 and the second imaging device 216 have fields of view which are separated from each other such that a person cannot be in both fields of view at the same time (e.g., adjacent). However, in some examples, first imaging device 210 and second imaging device 216 can have overlapping fields of view. It can be advantageous to have overlapping fields of view as processor 228 can use both first imaging device 210 and second imaging device 216 to track persons moving from primarily one field of view to the other field of view.

In some examples, the first imaging device 210 can have a first depth of field and the second imaging device 216 can have a second depth of field. In some such examples, the first imaging device 210 with the first depth of field can receive infrared image data at a first range of distances from the first imaging device 210. Further, in some such examples, the second imaging device 216 with the second depth of field can receive infrared image data at a second range of distances from the second imaging device 216. In some examples, the second depth of field is smaller than the first depth of field, and in some examples, the second range of distances is smaller than the first range of distances. A larger depth of field with a larger range of distances can allow the first imaging device to receive more infrared image data from a scene which includes multiple persons. However, a smaller depth of field with a smaller range of distances can allow the second imaging device to receive more focused infrared image data which can also be more accurate. In some examples, the depth of field of the first imaging device and the second imaging device can be adjusted. In some examples, the second imaging device has a higher resolution than the first imaging device.

Additionally, in some examples, second imaging device 216 can have a shorter minimum focus distance and a longer lens effective focal length than first imaging device 210. A shorter minimum focus distance and longer lens effective focal length can allow objects such as a person to be in focus at a distance closer to the imaging device. It can be advantageous to have objects such as a person be closer to second imaging device 216 as image data, such as IR light image data which corresponds to temperatures of the objects, can be more accurate than if objects are further away from the second imaging device 216. In FIG. 2, ETRS 224 and backdrop 226 are also within the field of view of second imaging device 216. Backdrop 226 can increase the accuracy and/or consistency of IR light image data received by second imaging device 216 as it can reduce noise generated by other heat sources and/or provide a constant background for imaging. ETRS 224 and backdrop 226 can also increase the accuracy of IR light image data received by second imaging device 216 and the accuracy of the temperature associated with the IR light image data as is described further herein. Thus, in some embodiments, the determined temperature in the high-accuracy screening area is more accurate than the determined temperature in the high-throughput screening area.

Continuing with the operation of FIG. 2, once a person 240 is within high-accuracy screening area 204 and in the field of view of second imaging device 216, second imaging device can receive IR light energy and in some examples, visible light energy, representative of the scene which includes person 240. Second imaging device 216 can generate IR light image data and in some examples, visible light image data from the received energy. From the IR light image data and optionally, visible light image data, second imaging device can determine temperatures associated with the scene. In some examples, processor 228 determines the temperatures associated with the scene from the IR light image data and optional visible light image data. Processor can receive the temperatures of the scene, including the temperatures associated with person 240, and determine if they exceed a temperature threshold. For example, processor can receive temperatures of the scene, determine the highest temperature within the scene that is associated with person 240, and compare it to the temperature threshold. If the temperature or temperatures associated with person 240 do not exceed the temperature threshold, processor 228 can operate second access gate 208 and allow person 240 to pass through. If the temperature or temperatures associated with person 240 exceeds the temperature threshold, processor 228 can provide a signal to indicator 234 which provides visual or other indication that the temperature associated with person 240 exceeds the temperature threshold. Additionally, in some examples, if the temperature or temperatures associated with person 240 exceed the temperature threshold, processor 228 can provide an indication that the one or more persons should be directed to a physical screening area (e.g., screening with an oral thermometer).

The configuration of the temperature scanner system of FIG. 2 can be advantageous because it uses multiple imaging device (e.g., 210, 216) to determine temperatures of persons. In such a configuration, different imaging devices can be used with the first imaging device 210 used in high-throughput screening area 202 being able to determine temperatures quickly with the second imaging device 216 used in high-accuracy screening area 204 being able to determine temperatures more accurately than first imaging device 210.

Figure 3:
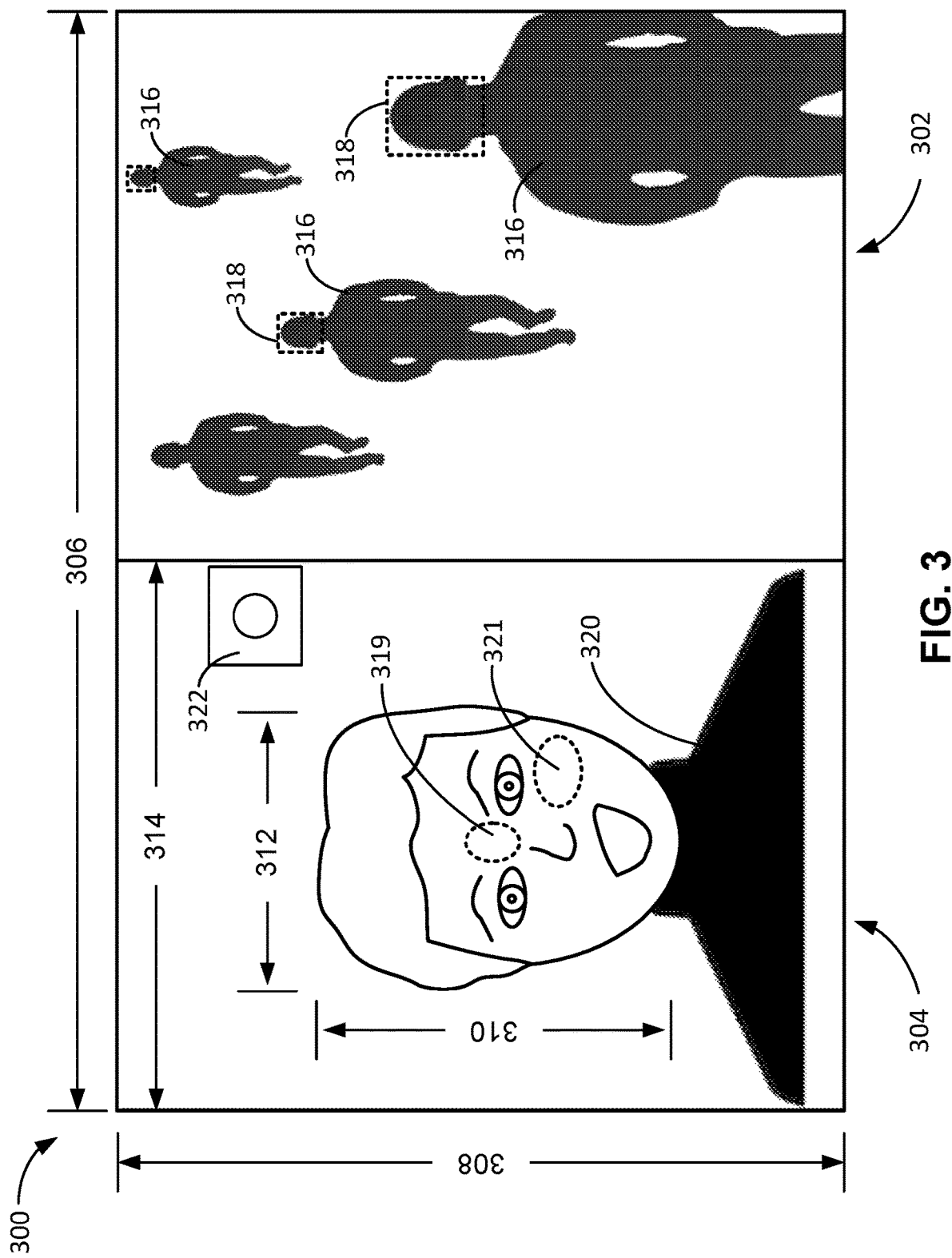
FIG. 3 is an example conceptual illustration of persons in a first target scene and second target scene as captured by an imaging device according to an aspect of the present disclosure.

FIG. 3 is an example conceptual illustration of persons in a first field of view 302 and a second field of view 304 as captured by one or more imaging devices according to an aspect of the present disclosure. The illustration of persons in the first field of view 302 and second field of view 304 includes pixel measurements 306, 308, 310, 312, and 314. FIG. 3 further includes persons 316 with heads and faces 318 and individual person 320 located in the second field of view 304. An ETRS 322 is also included and located in the second field of view 304. The first field of view can be a high-throughput screening area and the second field of view can be a high-accuracy screening area.

As shown in FIG. 3, multiple persons 316 can be located within the first field of view 302 as captured by one or more imaging devices (e.g., 110 of FIG. 1). As previously described, in operation, the one or more imaging devices can generate imagery data including image data representative of the persons 316 shown in the first field of view 302 while a processor can analyze the imagery data. Analyzing the imagery data can include using facial detection or recognition on the imagery data to determine if there are persons within the first field of view and/or where a person's head and/or face might be located within the image captured by the imaging device. As shown in the first field of view 302, persons 316 can be identified as a person and can be further identified as having a head and/or face 318. In some embodiments, the persons 316 can be identified as persons by the system identifying the persons' heads and/or faces. The processor can determine if a face is in the field of view 302 at different distances from the imaging device with the persons stationary or moving relative to the imaging device. In some examples, the processor can determine if a face is in the image even if the person is not facing the imaging device. Persons can generally move toward the imaging device and become larger in the field of view 302 and the processor can track the movements of the persons 316 along with their head and/or faces 318.

In some examples, within the first field of view 302, the processor, in combination with the imaging device, can further identify one or more specific portions of persons 316. In some examples, a specific portion is the face 318 of the persons. However, in some examples, the processor can identify portions of the face such as an eye or portion of the eye. In some examples, the processor can determine a temperature associated with a specific portion of the person and in some examples, the processor can further track the temperature of the specific portion of the person over time (e.g., while the person is moving). In some examples, the processor can have a higher accuracy when determining the temperature of a specific portion of the face (e.g., eye tear duct/inner canthus) than an entire face of the person.

In some examples, within the second field of view 304, the processor, in combination with the imaging device, can further identify one or more specific portions of the person 320. In some examples, a specific portion is the face of the person 320. However, in some examples, the processor can identify portions of the face such as an eye or forehead. In some examples, the processor can determine a temperature associated with a specific portion of the person and in some examples, the processor can further track the temperature of the specific portion of the person over time (e.g., while the person is moving). In some examples, the processor can have higher accuracy when determining the temperature of a specific portion of the face (e.g., eye tear duct/inner canthus) than an entire face of the person.

Continuing with the example of FIG. 3, the second field of view 304 can include a person in the high-accuracy screening area and captured by one or more imaging devices. In the second field of view, image data representative of an individual person 320 is displayed. A processor, in combination with the one or more imaging devices, can determine facial features of the individual person 320. Additionally, the processor and imaging devices can determine a temperature of the individual person 320 as previously described. In some examples, for the temperature of the individual person 320 to be considered a high-accuracy reading, a specific size of the head and/or face of the individual person 320 is required. For example, one such size requirement is shown in FIG. 3 by elements 310 and 312. Element 310 can be a minimum number of pixels corresponding to the height of the individual person's head and/or face and element 312 can be a minimum number of pixels corresponding to the width of the individual person's head and/or face. In some such examples, the pixels correspond to individual infrared sensors of an infrared sensor array of an imaging device. For example, a person's head can take up a number of pixels of the infrared sensor array. In some examples, a head and/or face of a person in a second target scene (e.g., high-accuracy screening area 104) is represented by more pixels than the head and/or face of a person in the first target scene (e.g., high-throughput screening area 102). In some examples, element 310 is at least 240 pixels and element 312 is at least 180 pixels. In some examples, the number of pixels can be higher or lower. Further, in some examples, a minimum number of pixels corresponding to the height of the entire image of the individual person (e.g., 308) and a minimum number of pixels corresponding to the length of the entire image of the individual person (e.g., 314) can be required for accuracy. For example, element 308 can be 320 pixels minimum and element 314 can be 240 pixels, although these pixel counts may be transposed if the imaging device is switched from portrait mode, as shown, to landscape mode. Certain standards, such as IEC 80601-2-59 or ISO/TR 13154, may require a 320×240 minimum pixel count. Other pixel counts (e.g., 480×320) for accuracy may be used.

As depicted in FIG. 3, a first region 319 may comprise a facial region of the individual person 320 located between the individual's eyes and a second region 321 may comprise a cheek region of the individual person 320. A first surface temperature for the first region 319 may be determined using an average temperature for pixels within a thermal image corresponding with the first region 319. A second surface temperature for the second region 321 may be determined using an average temperature for pixels within the thermal image corresponding with the second region 321. A first temperature offset may be acquired and used to estimate a first internal core temperature and a second temperature offset may be acquired and used to estimate a second internal core temperature. In at least one example, an internal core temperature may be computed as an average of the first internal core temperature and the second internal core temperature. In another example, an internal core temperature may be determined as the highest temperature out of the first internal core temperature and the second internal core temperature.

While persons' head and/or faces have been described as being used, other parts of persons may be used to identify, track, and/or determine the accuracy of a temperature reading of the persons. For example, in some embodiments, the system uses a person's head to identify the person and uses the person's head to track the person throughout a target scene.

Continuing with FIG. 3, an ETRS 322 is included in second field of view 304. ETRS 322 is an external temperature reference source which can help an imaging device and/or a processor determine a temperature of objects in a scene. ETRS 322 of FIG. 3 is active, but in some examples, ETRS can be passive. ETRS 322 can have a temperature sensor connected to the surface (e.g., control plate) of the ETRS measuring the temperature of the ETRS. Further, ETRS 322 can have control circuitry to maintain the temperature of the surface of the ETRS at substantially a constant level. In some examples, the surface of the ETRS has known parameters such as emissivity. By using the temperature and the known parameters of the surface, the imaging device and/or the processor can correlate IR light image data corresponding with the ETRS with the known temperature from the temperature sensor. This can help calibrate and increase the accuracy of the determined temperature of persons within the same field of view. Additionally, in some examples, the temperature of the ETRS can be set approximately to a threshold temperature (e.g., elevated temperature) which can further increase accuracy because it can minimize any response and/or gain error contributions from the imaging device.

In some examples, multiple ETRS are used to further increase the accuracy. In some examples, a single ETRS can be used between multiple scenes (e.g., the ETRS of FIG. 1). In further examples, an ETRS can be used only for a high-accuracy screening area while no ETRS is used for a high-throughput screening area. In some examples, when using an ETRS, it can be more accurate to have the subject (e.g., a person) be at the same distance from the imaging device as the ETRS is from the imaging device. In these examples, the temperature of the ETRS is mostly unaffected by any other sources and the IR light received by the imaging device travels substantially the same distance to the imaging device from both the ETRS and the subject. This configuration can reduce atmospheric interference on the temperature reading of the subject. In some examples, the ETRS is behind the subject so that the subject does not substantially affect the temperature of the ETRS (e.g., by breathing on it).

In some examples, imagery, temperatures, and other data (e.g., a confidence factor) can be displayed on a display. Imagery data can include visible light imagery and/or infrared light imagery. In some such examples, the display can display information about each individual person proximate to the imagery of said person. In some examples, the display is monitored by an operator such that if a person has a temperature above the threshold, the operator can notify the person, and if a person has a temperature below the threshold, the operator can allow access through access gates. However, in some examples, the display is not actively monitored by an operator and displays information to any person such as the persons being screened. More than one display can be used, however in some examples, one display is used which incorporates one or more imaging devices. For example, FIG. 3 can be an example view of a display as it displays multiple fields of view from multiple imaging devices and can also be an example view of a display as it displays a single field of view from a single imaging device.

As previously discussed herein, one or more imaging devices in communication with a processor can determine the temperature of one or more persons in a target scene. However, in some examples, a confidence factor is included with the determining of the temperature of one or more persons. A confidence factor, as used in this disclosure, is a measurement of certainty/uncertainty. For example, the confidence factor can be a determination of the likelihood that something, such a measurement, value, or series of values, is accurate. In at least one example, a large uncertainty range can indicate a lower confidence factor while a small uncertainty range can indicate a higher confidence factor. The confidence factor can be an additional step in determining the temperature of one or more persons and can be used to increase the accuracy of any temperature determinations of the persons. In some examples, the confidence factor can be associated with an image or series of images which can include IR light image data and/or visible light image data. In some examples the confidence factor can be associated with a temperature or series of temperatures which can be determined from IR light image data and optionally, visible light image data. In operation, a confidence factor is determined by a processor (e.g., processor 228 of FIG. 2) and can be compared to a threshold. In some examples, more than one confidence factor can be used with each confidence factor comprising multiple other factors.

The confidence factor can include many individual factors which are specific to the determination being done. In some examples, the confidence factor can have individual factors related to the specific properties of an image such as the clarity, blurriness, brightness, darkness, and contrast. In some examples, the confidence factor can be weighted. In some examples, the confidence factor can take into account multiple images over a period of measurement. In some such examples, the confidence factor can include an analysis of the multiple images (e.g., average amount of clarity and/or brightness). In one such example, a first confidence factor can be assigned to a first image (e.g., frame) of a plurality of images (e.g., a video) and a second confidence factor can be assigned to a second image of the plurality of images. Each of the first and the second confidence factors can be weighted based on distance from the person to the imaging device and an overall confidence factor can be aggregated from the first and second confidence factors. An overall confidence factor (e.g., aggregated confidence factor) can be compared and used in any case where an individual confidence factor is used (e.g., compared to a threshold). In some examples, the confidence factor can have individual factors related to the objects within the image such as the number of persons or properties of the persons. For example, a confidence factor can include the likelihood that a person has one or more obstructions on their face which interfere with the temperature determination. Some examples of obstructions include hair, glasses, hats, and masks. These obstructions could affect the accuracy of the temperature determination of the person. In some other examples, a confidence factor can include the distance between a person whose temperature is being determined and the imaging device generating the image data of the person. Because the distance can affect the temperature determination of the person, a confidence factor can be assigned to the temperature determination which takes into account that smaller distances from an imaging device generally produce more accurate temperature determinations than larger distances from an imaging device. In some examples, a confidence factor can include the direction a person is facing and a speed at which the person is moving. The confidence factor can include any number of the factors above and other factors not listed.

In some example operations, a relatively low confidence factor can be associated with/assigned to a temperature reading of a person's face due to the temperature reading of their face being below a threshold. The temperature reading being below a threshold could indicate that some obstruction is located on the person's face and the relatively low confidence factor can reflect that it is likely some obstruction is preventing a more accurate temperature reading. In such a case, an initial confidence factor can be 100% and is subsequently lowered by 20% to be 80% due to the person's temperature being below a threshold. In some other example operations, a relatively low confidence factor can be associated with/assigned to a temperature reading of a person's face due to the person not looking toward the imaging device. The relatively low confidence factor can thus reflect the likelihood that the temperature reading of the person's face is accurate due to the positioning of the person's face. In such a case, an initial confidence factor can be 100% and is subsequently lowered by 30% to be 70% due to the person not looking toward the imaging device. Other factors are contemplated, and different factors can have different impacts on the confidence factor. For example, a person not looking toward the imaging device as well as their temperature being below a threshold could lower the confidence factor from 100% to 50% with each factor contributing to the decrease in the confidence factor. In some examples, factors add together to decrease the confidence factor as described above, while in some examples, factors can be combined in a non-linear fashion. One such example of a non-linear combination is that one factor contributes to a decrease of 10% in the confidence factor by itself and another factor contributes to a decrease of 15% by itself. However, when both factors are present, the confidence factor can decrease by 50%. Other examples of confidence factors, other combinations of factors, and other contributions of the factors to the confidence factor are contemplated and this disclosure is not limited to the examples above.

In some examples, the confidence factor can change over time. In some such examples, the confidence factor can change over time based on the temperature determination changing over time. A processor can change the confidence factor over time based on information or factors which were not previously used in the confidence factor. For example, the confidence factor associated with a temperature determination of a person can increase continuously as a person gets closer to an imaging device as the imaging device can receive more IR light from the person and/or the imaging device can obtain finer details of the person. It can be advantageous to continually update a confidence factor as it can increase the accuracy of determinations such as a temperature determination.

In some example operations, a confidence factor can change as the imaging device receives images. In one such example operation, a confidence factor can be associated with/assigned to a first image in which the person's face is blurred due to their head motion. Subsequently, the confidence factor can be updated to reflect a second image in which the person's face is clear (e.g., not blurred). In some examples, the updating can be an aggregate of individual confidence factors associated with/assigned to a temperature reading, while in some examples, the updating can be a running average. Other methods of analysis and updating of the confidence factor are contemplated.

In some examples, the confidence can be compared to a threshold by a processor. If the confidence factor does not exceed a threshold, the processor can perform an additional action, such as providing a signal that the confidence factor did not exceed the threshold. In some examples in which a confidence factor is based on the accuracy of the determined temperature of a person, the confidence factor not exceeding its threshold, the determined temperature exceeding a threshold, or a combination thereof, can be used to indicate the person needs further screening. For example, a person can have a temperature determined in a high-throughput screening area which is within an acceptable range, however, an associated confidence factor can be lower than a threshold, indicating that the determined temperature is not sufficiently accurate. In such an example, the person can be directed to a high-accuracy screening area for further temperature determination.

Figure 4:
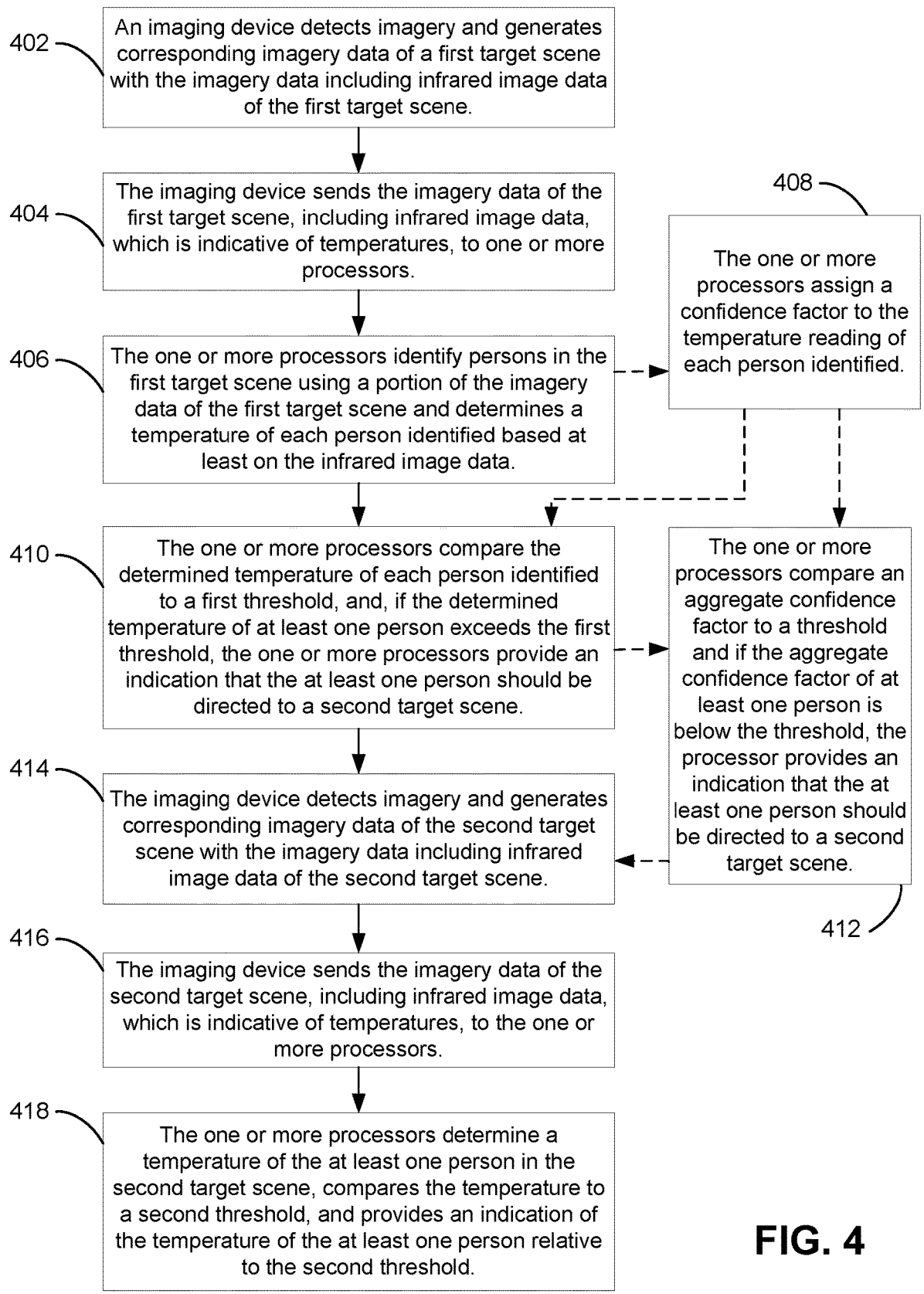
FIG. 4 is an example flow diagram of a method of scanning temperatures of persons according to an aspect of the present disclosure.

FIG. 4 is an example flow diagram of a method of scanning temperatures of person according to an aspect of the present disclosure. The method starts with 402, in which an imaging device detects imagery and generates corresponding imagery data of a first target scene. In some examples, the first target scene can include one or no persons. The method continues with step 404 in which the imaging device sends imagery data of the first target scene, including infrared image data, which is indicative of temperatures, to one or more processors. Next, in step 406, the one or more processors identifies persons in the first target scene using imagery of the scene and determines a temperature of each person identified. In some examples, the method continues with step 410, however, in some examples, optional step 408 is performed. In step 408, the processor assigns a confidence factor to the determined temperature of each person identified. In some embodiments, the confidence factor is assigned based on imagery data of the first target scene. From optional step 408, the method can either continue with step 410 or, optionally, to step 412. In step 410, the one or more processors compare the determined temperature of each person identified to a first threshold. If the determined temperature of at least one person exceeds the first threshold, the one or more processors is configured to provide an indication that the at least one person should be directed to a second target scene. From step 410, the method can either continue with step 414 if the determined temperature of at least one person exceeds the first threshold, or optionally, with step 412, regardless of the result of the comparison. In optional step 412, the one or more processors compare an aggregated confidence factor to a threshold confidence factor and if the determined confidence factor of at least one person is below the threshold, the processor provides an indication that the at least one person should be directed to a second target scene. From 412, the method continues with step 414 if the aggregated confidence factor is below the threshold. In step 414, the imaging device generates imagery data of the second target scene with the imagery data including infrared image data of the second target scene. Next, in step 416, the imaging device sends the imagery data of the second target scene, including infrared image data, which is indicative of temperatures, to the one or more processors. In step 418 of the example of FIG. 4, the one or more processors determine a temperature of the at least one person in the second target scene, compares the temperature to a second threshold, and provides an indication of the temperature of the at least one person relative to the second threshold. While the steps above are described as happening sequentially, in some examples, some steps of the method can be done simultaneously and, in some examples, some steps can happen before or after other steps. For example, the second imaging device can generate IR image data of the second target scene before, after, or during when the first imaging device generates IR image data of the first target scene.

Figure 5:
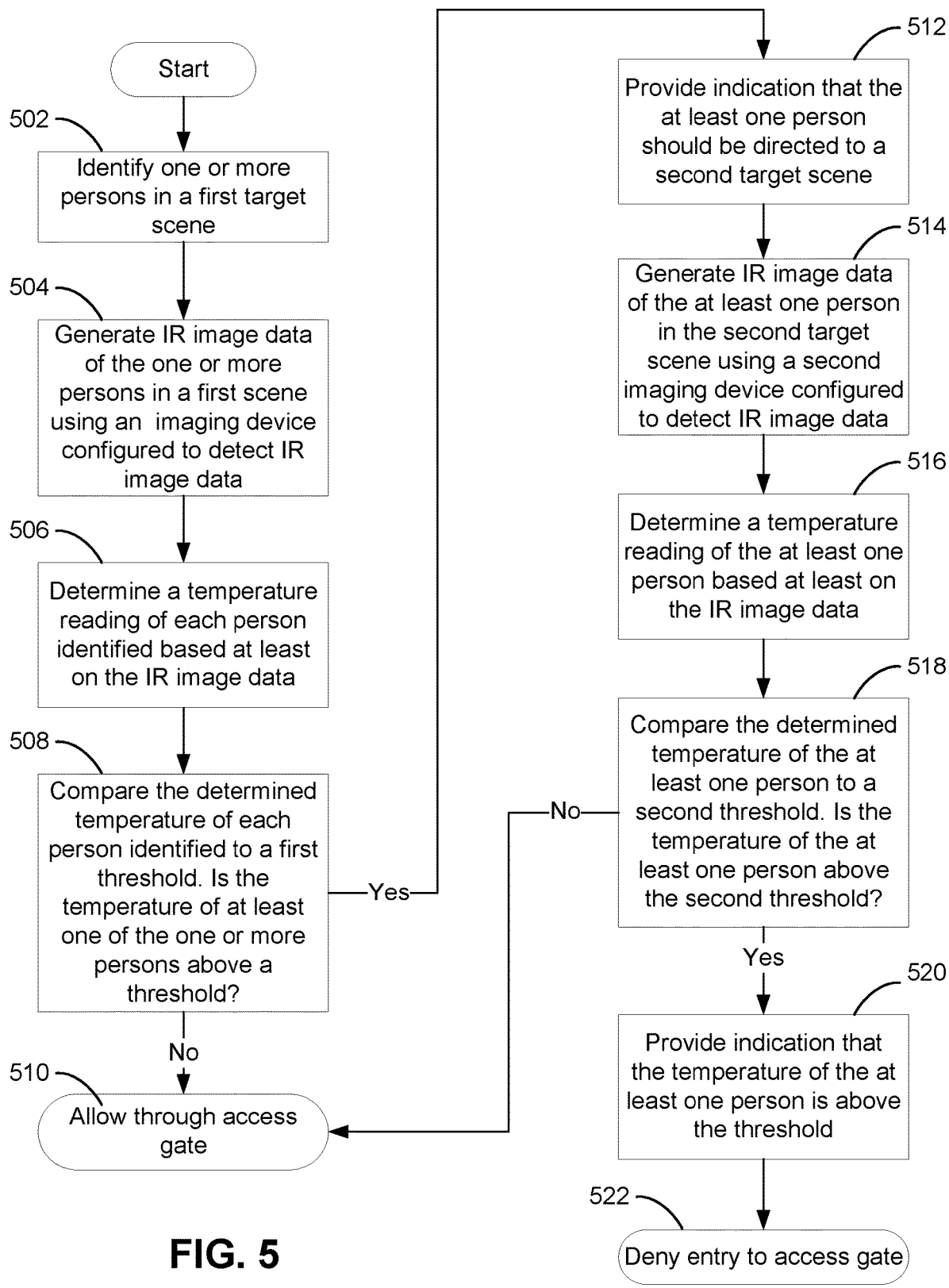
FIG. 5 is an example flow diagram of another method of scanning temperatures of persons according to an aspect of the present disclosure.

FIG. 5 is an example flow diagram of another method of scanning temperatures of person according to an aspect of the present disclosure. The method starts with step 502, in which one or more persons are identified in a first target scene. Next, in step 504, an imaging device configured to detect IR energy generates IR image data of the one or more persons in a first scene. Further, in step 506, a temperature reading of each person identified is determined based at least on the IR image data. Next, in step 508, the temperature of each person identified is compared to a threshold. In the case that each person identified has a temperature below a threshold, each person is allowed through an access gate as in step 510. In the case that at least one of the one or more persons has a temperature reading above the threshold, the method continues with step 512. In step 512, an indication is provided that the at least one person should be directed to a second target scene. Continuing with step 514, the imaging device generates IR image data of the at least one person in the second target scene. Next, in step 516, a temperature reading of the at least one person is determined based at least on the IR image data. Further, in step 518, the determined temperature of the at least one person is compared to a second threshold. In the case that the temperature of the at least one person is not above the threshold, the at least one person is allowed through the access gate as in step 510. If, however, the temperature of the at least one person is above the threshold, the process continues with step 520. In step 520, an indication is provided which indicates the temperature of the at least one person is above the threshold. In some optional embodiments, the method can continue with denying entry to the at least one person through the access gate as in step 522. While the steps above are described as happening sequentially, in some examples, some steps of the method can be done simultaneously, and in some examples, some steps can happen before others. For example, the comparison of step 508 can be happening simultaneously with the comparison of step 518.

In some examples of the system for screening persons for elevated temperatures, processes for adjusting the determining of temperature readings can be included. In some such examples, a processor, which determines the temperatures of the persons in the target scene, can adjust the determined temperatures based on previous determinations. For example, a processor can determine the temperatures of persons in a first target scene using IR image data of the first target scene. The processor can later adjust and determine the temperatures of persons in the first target scene, however, the temperatures determined later can be higher and/or lower than they would have been if the processor had not adjusted. In at least one example, the temperatures of the persons all exceed the threshold and the processor adjusts such that the temperatures of the same persons no longer exceed the threshold. In some examples, the adjustment can be temporary (e.g., for a determined amount of time) while in some examples, the adjustment can be permanent until subsequent adjustment.

In some examples, the determined temperature readings of the second scene are used to adjust the determining of temperature readings of the first scene. For example, if determined temperatures of a majority of individuals in the second scene do not exceed a threshold, the processor can be adjusted to change its determination of temperatures of individuals in the first scene. In this example "false positives," where an individual is directed to a second scene due to their temperature exceeding a threshold in the first target scene, can be reduced. Further, in some examples, the temperature of individual persons relative to an average temperature of a plurality of persons is used to adjust the system. In some such examples, the processor can determine if a temperature of a person is different than previous temperatures of persons. In some examples, adjustment can be done while the system for screening persons is active (e.g., continuous adjustment). Further, adjustment, as described above, can be applied to the threshold in addition to or in lieu of adjusting the determining of the temperature. In some examples, directing random persons to go from the high-throughput screening area to the high-accuracy screening area can aid in adjusting various portions of the screening system including the threshold. The random directing of persons to the high-accuracy screening area can prevent large variations between the first scene and second scene temperatures and can increase accuracy of both. In some examples, the directing of person to the high-accuracy screening area is not random and can vary based on a number of factors including the number of persons and the frequency of which persons are required to go through the high-accuracy screening area. In some examples, the threshold can be adjusted in response to outdoor temperatures. Adjusting the threshold for outdoor temperature can be advantageous as persons can have increased/decreased temperatures for a period of time after entering a screening area from the outside. It can also be advantageous to adjust temperature determinations and/or thresholds because persons can have a range of temperatures which can be considered "normal" (e.g., one person has a higher "normal" temperature than another person). Additionally, it can be advantageous to adjust temperature determinations and/or thresholds because portions of the system, including the imaging device(s) used to generate IR image data, can be subject to unintentional changes (e.g., temperature changes) over time.

In some examples of the system for screening persons for elevated temperatures, data, which can include IR image data, temperature data, and confidence factor data, can be correlated between data obtained from a high-throughput area and data obtained from a high-accuracy area. In some such examples, a processor can correlate and/or analyze the data. The processor can use the data to determine various aspects of the system. For example, if the imaging device of the high-throughput area identifies an individual person with a temperature exceeding a threshold, the imaging device of the high-accuracy area can identify if the same individual is in the high-accuracy area (e.g., facial recognition). The data can then be linked for later use such as for adjustment of the system. In such an example, the system can determine that a person has been through the high-accuracy area before allowing the person through an access gate. In some examples, the data from the high-throughput area and data from the high-accuracy area are correlated such that the process of assigning a confidence factor in the high-throughput area is updated during operation. Other examples of using correlated data are contemplated including using the correlated data to adjust the temperature determinations of the imaging devices and using the correlated data to adjust the threshold. A person having ordinary skill will appreciate that the disclosure is not limited to the examples above.

In further examples of the system for screening persons for elevated temperatures, data (e.g., IR image data) can be used from both the high-accuracy screening area and the high-throughput screening area for later analysis and updating of algorithms. Algorithms can include algorithms for correlating IR image data with temperatures and algorithms for determining threshold temperatures. For example, machine learning can be used with the data collected by the first imaging device and the second imaging device to adjust later, or in real time, screening parameters of the first imaging device or of the processor. Other methods for analyzing the data and adjusting various parameters of the screening system are contemplated.

Figure 6:
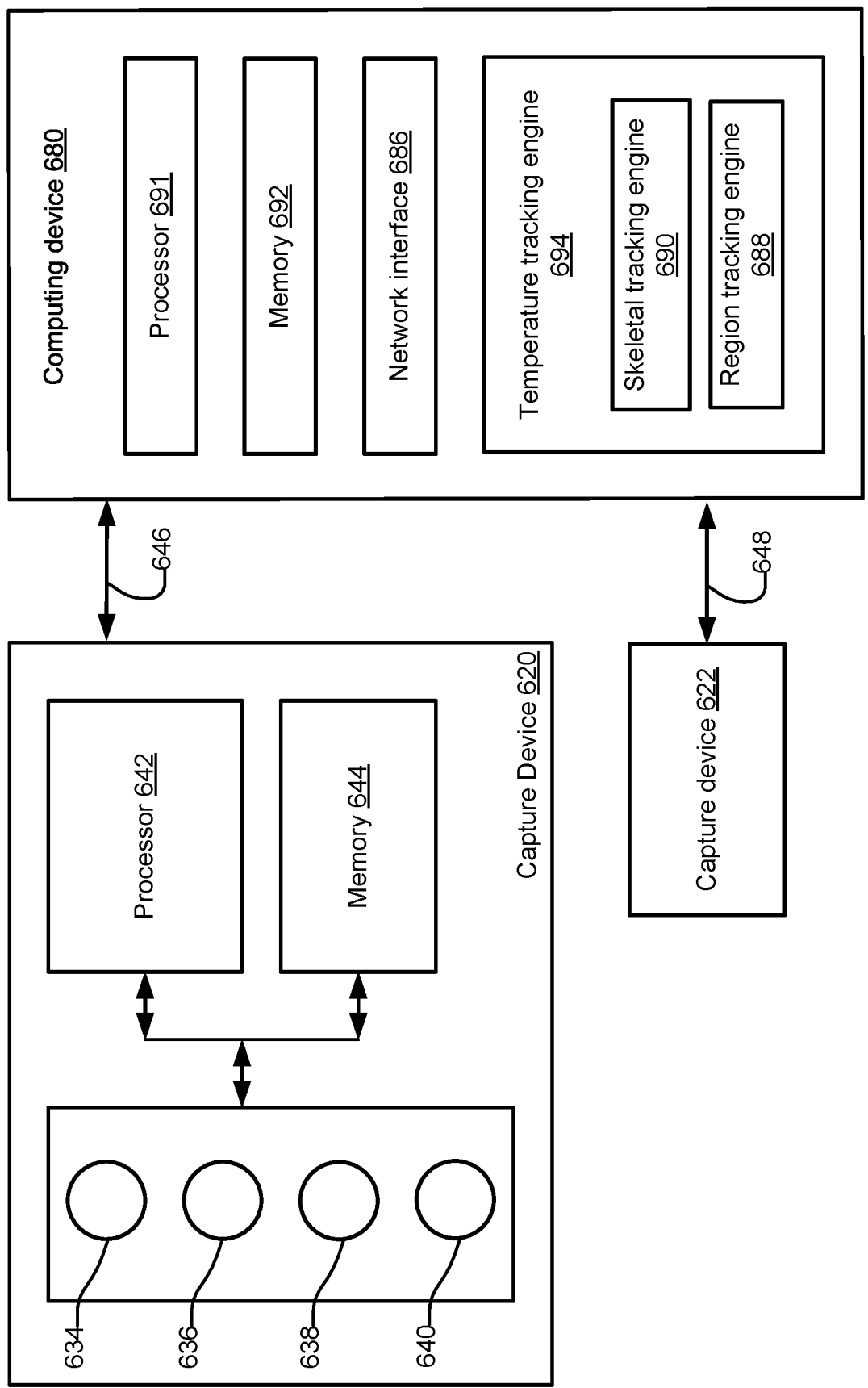
FIG. 6 depicts an embodiment of a computing device in communication with two capture devices, such as two different thermal imaging cameras.

FIG. 6 depicts an embodiment of a computing device 680 in communication with a capture device 620 and a capture device 622. The capture device 620 and the capture device 622 may comprise thermal image capturing devices. In some embodiments, capture device 620 and computing device 680 may be integrated together within a common housing. In other embodiments, the capture device 620 may comprise a thermal image capturing device and the computing device 680 may be in communication with the capture device 620 via a wired or wireless networking connection. The capture device 620 may be in communication with the computing device 680 via a networking path 646. The capture device 622 may be in communication with the computing device 680 via a networking path 648. The networking path 646 and the networking path 648 may be formed via one or more networks not depicted that may include a cellular network, a mobile network, a wireless network, a wired network, a secure network such as an enterprise private network, an unsecure network such as a wireless open network, a local area network (LAN), a wide area network (WAN), the Internet, or a combination of networks. Each network of the one or more networks may include hubs, bridges, routers, switches, and wired transmission media such as a wired network or direct-wired connection. In some embodiments, the computing device 680 may comprise a real hardware computing device with real hardware processors and storage devices or a virtual computing device that includes one or more virtual machines. The real hardware storage devices may include non-volatile and volatile storage devices.

In at least one embodiment, the capture device 620 may include one or more image sensors for capturing images. An image sensor may comprise a CCD image sensor or a CMOS image sensor. In some embodiments, capture device 620 may include a thermal image sensor and/or an IR CMOS image sensor. The capture device 620 may include an IR light component 634 for a depth camera, a depth camera 636, an RGB camera 638, and a thermal camera 640. In at least one example, the IR light component 634 may emit an infrared light into a capture area and may then use sensors to detect the backscattered light from the surface of one or more individuals in the capture area using the color and/or IR light sensing components within the capture device 620. In some embodiments, pulsed infrared light may be used such that the time between an outgoing light pulse and a corresponding incoming light pulse may be measured and used to determine a physical distance from the capture device 620 to a particular region on a surface of an individual within the capture area. Capture device 620 may also include optics for producing collimated light and/or for diffusing light (e.g., an optical diffuser for spreading light from an IR light source that generates a narrow beam of light) for illuminating an environment.

As depicted in FIG. 6, the capture device 620 may include a processor 642, which may include a hardware processor or a microprocessor, and a memory 644. The processor 642 may execute instructions stored within memory 644 for tracking regions (or exposed skin surface regions) of individuals within the capture area and determining temperatures for the tracked regions. The memory 644 may include random access memory (RAM), read only memory (ROM), cache, Flash memory, a non-volatile memory, or any other suitable storage component. The capture device 620 may detect a tracked region using captured color images and then determine a temperature for the tracked region using captured thermal images. The capture device 620 may output or transfer temperature information for the tracked regions to the computing device 680.

As depicted in FIG. 6, computing device 680 includes a processor 691, a memory 692, a network interface 686, and a temperature tracking engine 694 all in communication with each other. Network interface 686 allows computing device 680 to connect to one or more networks and/or one or more capture devices, such as capture devices 620 and 622. Network interface 686 may include a wireless network interface and/or a wired network interface. Processor 691 allows computing device 680 to execute computer readable instructions stored in memory 692 in order to perform processes discussed herein. Processor 691 may include one or more processing units, such as one or more CPUs and/or one or more GPUs. Memory 692 may comprise one or more types of memory (e.g., RAM, SRAM, DRAM, ROM, EEPROM, or Flash). Memory 692 may comprise a hardware storage device or a data storage device. The processor 691 and memory 692 may be configured to allow the computing device 680 to acquire thermal image information, color image information, and/or depth information from one or more capture devices and to process the acquired image information to track temperatures for regions of individuals within a temperature screening area. The image information may be used by the processor 691 to track one or more regions of an individual over time, determine temperatures for the one or more regions, and determine temperature measurement confidence values corresponding with the determined temperatures. The temperatures for the one or more regions and the temperature measurement confidence values may be stored within memory 692 or using a lookup table located on a data storage device. In at least one example, the computing device 680 may track a forehead region of an individual and a temporal region of the individual and store temperature data for the tracked regions on a periodic basis (e.g., every minute).

The temperature tracking engine 694 includes a skeletal tracking engine 690 and a region tracking engine 688. The skeletal tracking engine 690 may leverage a skeletal model of a human to help recognize body parts (e.g., arms, hands, and faces). The region tracking engine 688 may track one or more regions of an individual using image information acquired from capture devices 620 and 622. The region tracking engine 688 may use thermal image information, color image information, and/or depth information in order to detect a particular facial region of an individual and determine a surface temperature for the particular facial region. In the event that the particular facial region is determined to be obstructed due to people or objects within an environment blocking a view of the particular facial region, due to the individual facing away from a capture device, or due to the presence of a wearable obstruction to the particular facial region (e.g., a face mask), the region tracking engine 688 may delay storing temperature information for the particular facial region until reliable temperature information for the particular facial region is acquired.

Figure 7A:
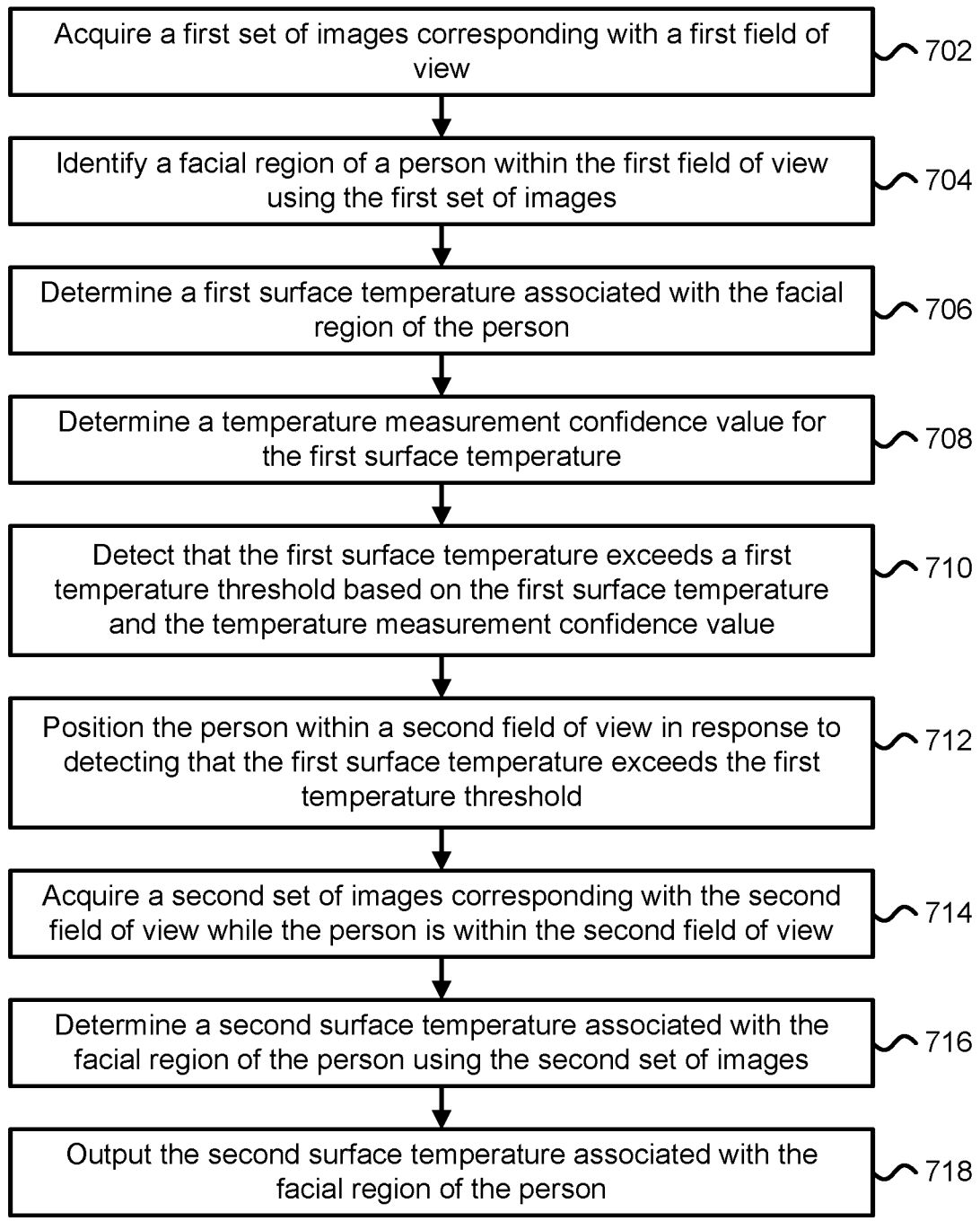
FIG. 7A depicts a flowchart describing an embodiment of a process for identifying individuals that have exposed skin surface temperatures outside of a range of approved temperatures.

FIG. 7A depicts a flowchart describing an embodiment of a process for identifying individuals that have exposed skin surface temperatures outside of a range of approved temperatures. In at least one embodiment, the process of FIG. 7A may be performed by a computing device, such as the computing device 680 in FIG. 6. In another embodiment, the process of FIG. 7A may be performed by a processor, such as processor 128 in FIG. 1 or processor 228 in FIG. 2. In some embodiments, the process or portions of the process of FIG. 7A may be performed using one or more virtual machines and one or more virtual storage devices.

In step 702, a first set of images corresponding with a first field of view (e.g., of a first imaging device) is acquired. In some cases, the first field of view may correspond with a field of view of a first imaging device, which may correspond with capture device 620 in FIG. 6, imaging device 110 in FIG. 1, or first imaging device 210 in FIG. 2. The first set of images may include color images and thermal images. In step 704, a facial region of a person within the first field of view of a first imaging device is identified using the first set of images. In step 706, a first surface temperature associated with the facial region of the person is determined. In at least one example, the facial region of the person may correspond with a forehead region of the person and the first surface temperature may be derived from a thermal image that includes at least a threshold number of pixels covering the forehead region of the person. Each pixel in a thermal image may correspond with a temperature value for the pixel.

In step 708, a temperature measurement confidence value for the first surface temperature is determined. In at least one example, if it is detected that the person is within a threshold distance (e.g., within thirty feet from the first imaging device), then the temperature measurement confidence value for the first surface temperature may be set to 1.0; otherwise, if it is detected that the person is not within the threshold distance, then the temperature measurement confidence value for the first surface temperature may be reduced to a value less than 1.0 based on the distance between the first imaging device and the person. In another example, if it is detected that the person was moving or walking when the first set of images were captured and a speed of movement is less than a threshold speed (e.g., is less than 3 miles per hour), then the temperature measurement confidence value for the first surface temperature may be set to 1.0; otherwise, if it is detected that the speed of movement for the person at the time that the first set of images were captured is greater than or equal to the threshold speed, then the temperature measurement confidence value for the first surface may be set to a value less than 1.0 (e.g., to 0.7) based on the speed of movement.

In step 710, it is detected that the first surface temperature exceeds a first temperature threshold (e.g., is greater than 99 degrees Fahrenheit) based on the first surface temperature and the temperature measurement confidence value. In at least one example, if the temperature measurement confidence value is greater than 0.9 and the first surface temperature exceeds the first temperature threshold (e.g., the first surface temperature exceeds 99 degrees Fahrenheit), then it may be detected that the first surface temperature exceeds the first temperature threshold. If the temperature measurement confidence value is less than 0.7, then the corresponding surface temperature may be deemed to be unreliable and not used for determining whether the first surface temperature has exceeded the first temperature threshold.

In step 712, the person is positioned within a second field of view (e.g., of a second imaging device different from the first imaging device) in response to detecting that the first surface temperature exceeds the first temperature threshold. In some cases, both the first field of view and the second field of view may be captured using the same imaging device. An imaging device may correspond with capture device 622 in FIG. 6. In some cases, the first field of view may be wider than the second field of view. A reduced field of view or a narrower field of view may improve the accuracy of a temperature screening by capturing a greater number of pixels of a targeted region of the person. An imaging device may reduce its field of view in order to capture a greater number of pixels of a targeted region of the person. The second imaging device may acquire or capture higher resolution thermal images compared with the first imaging device. The second imaging device may adjust an optical zoom of the second imaging device in order to capture at least a threshold number of pixels covering the facial region of the person.

In step 714, a second set of images corresponding with the second field of view of a second imaging device is acquired while the person is within the second field of view of the second imaging device. In step 716, a second surface temperature associated with the facial region of the person is determined using the second set of images. In at least one embodiment, the second surface temperature may correspond with a portion of the facial region less than the entire facial region. For example, if the facial region of the person comprises a forehead region of the person, then the portion of the facial region may comprise a small region between the eyes of the person.

In at least one embodiment, a number of pixels for the facial region of the person captured by the first set of images may comprise a first number of pixels and the number of pixels for the facial region of the person captured by the second set of images may comprise a second number of pixels greater than the first number of pixels. The second surface temperature associated with the facial region of the person may be determined by averaging temperature values for the pixels covering the facial region or by averaging the three highest temperature values for the pixels covering the facial region. In step 718, the second surface temperature associated with the facial region of the person is outputted. The second surface temperature may be transmitted to another computing device, such as a mobile computing device or smart phone. The second surface temperature may be displayed using an electronic display. In some embodiments, an internal core temperature for the person may be estimated using the second surface temperature.

Figure 7B:
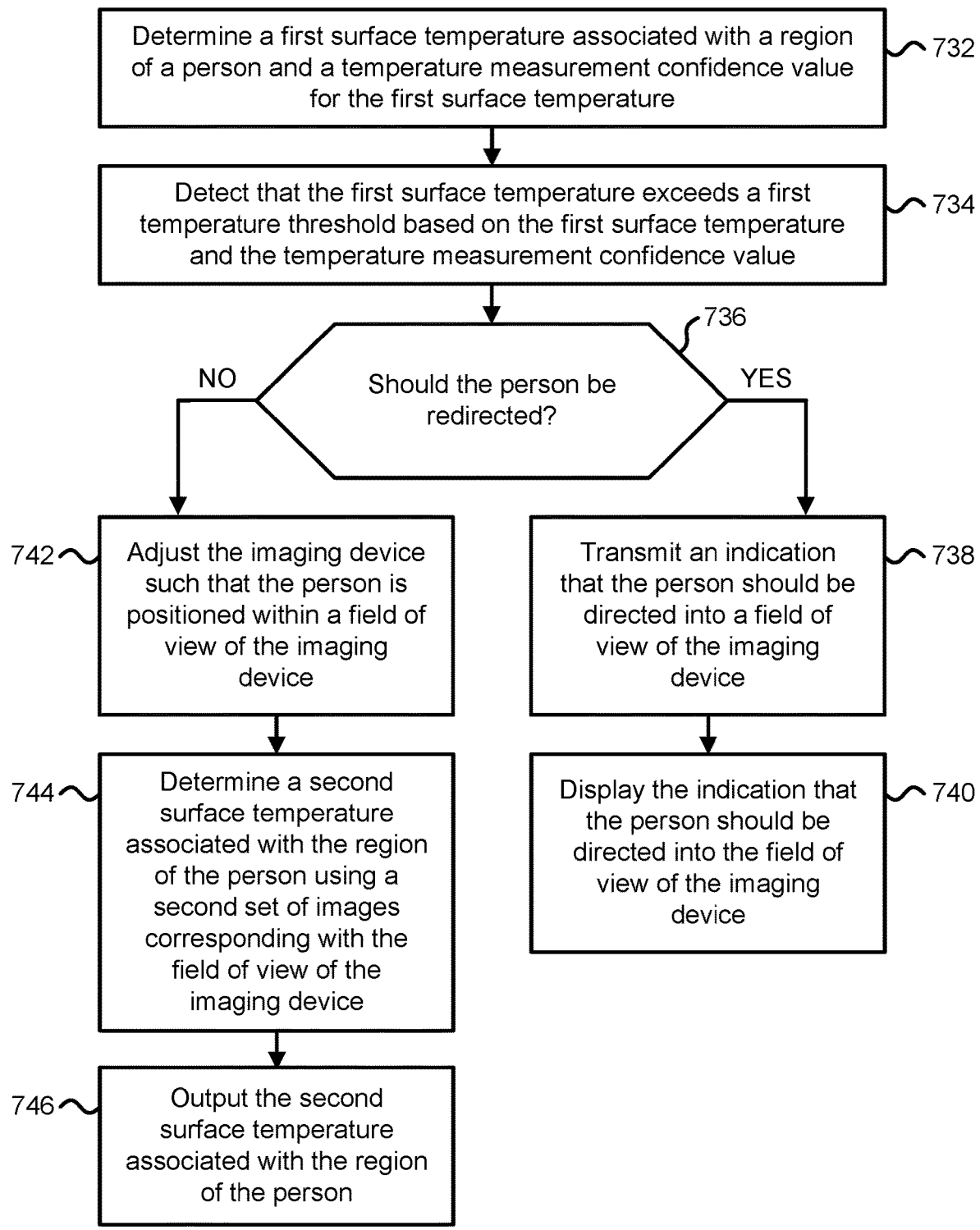
FIG. 7B depicts a flowchart describing another embodiment of a process for identifying individuals that have exposed skin surface temperatures outside of a range of approved temperatures.

FIG. 7B depicts a flowchart describing another embodiment of a process for identifying individuals that have exposed skin surface temperatures outside of a range of approved temperatures. In at least one embodiment, the process of FIG. 7B may be performed by a computing device, such as the computing device 680 in FIG. 6. In another embodiment, the process of FIG. 7B may be performed by a processor, such as processor 128 in FIG. 1 or processor 228 in FIG. 2. In some embodiments, the process or portions of the process of FIG. 7B may be performed using one or more virtual machines and one or more virtual storage devices.

In step 732, a first surface temperature associated with a region of a person (or a person) is determined. The region of the person may comprise a facial region or another region of the person's body, such as an exposed arm region or an exposed leg region. Along with the first surface temperature, a temperature measurement confidence value for the first surface temperature may be determined and stored. The temperature measurement confidence value may be determined based on a number of pixels covering the region of the person. In one example, the temperature measurement confidence value may comprise the number of pixels covering the region divided by 16. The temperature measurement confidence value may correspond with a confidence score or a reliability score for the first surface temperature. In at least one example, if a walking speed or a movement of the person at the time that the first surface temperature was captured was greater than a threshold speed, then the temperature measurement confidence value may be divided in half or set to 0.5; otherwise, the temperature measurement confidence value may be set to 1.0.

In step 734, it is detected that the first surface temperature exceeds a first temperature threshold based on the first surface temperature and the temperature measurement confidence value. It may be detected that the first surface temperature exceeded the first temperature threshold if the first surface temperature is greater than the first temperature threshold and the temperature measurement confidence value for the first surface temperature is greater than 0.7. In one embodiment, it may be detected that the first surface temperature exceeds the first temperature threshold (e.g., is greater than 99° F.) and that the temperature measurement confidence value exceeds a confidence value threshold (e.g., is greater than 0.7).

In some cases, an imaging device may be adjusted or reoriented in response to detecting that the first surface temperature exceeds a first temperature threshold and that the temperature measurement confidence value for the first surface temperature exceeds a confidence value threshold. In other cases, an imaging device may be adjusted or reoriented in response to detecting that the first surface temperature exceeds a first temperature threshold or that the temperature measurement confidence value for the first surface temperature is below a confidence value threshold.

In some embodiments, it may be determined whether an orientation of an imaging device should be adjusted or reoriented. In at least one embodiment, if the person is within a threshold distance of the imaging device, then the orientation of the imaging device will be adjusted to capture the region of the person. In another embodiment, if a speed of the person is less than a threshold speed, then the orientation of the imaging device will be adjusted to capture the region of the person.

In some embodiments, an imaging device may not be adjusted, reconfigured, or reoriented to position the person within a field of view of the imaging device if the person is redirected or moved to a designated location in front of the imaging device or otherwise positioned within the field of view of the imaging device.

In step 736, it is determined whether the person should be redirected or otherwise moved into a field of view of an imaging device. If it is determined that the person should be redirected into the field of view of an imaging device, then step 738 is performed. In step 738, an indication that the person should be directed or moved into the field of view of the imaging device is transmitted. In step 740, the indication that the person should be directed or moved into the field of view of the imaging device is displayed. In at least one example, the indication that the person should be directed into the field of view of the imaging device may be displayed by displaying textual instructions and/or symbols on a display screen. The display screen may comprise a display of a portable electronic device or a smart phone used by the person.

If it is determined that the imaging device should be adjusted or that the person should not be redirected into the field of view of the imaging device, then step 742 is performed. In step 742, the imaging device is adjusted such that the person is positioned within a field of view of the imaging device. The adjustment may comprise an orientation adjustment and/or an optical adjustment (e.g., adjusting an optical zoom) of the imaging device. In step 744, a second surface temperature associated with the region of the person is determined using a second set of images corresponding with the field of view of the imaging device. In step 746, the second surface temperature associated with the region of the person is outputted. In at least one embodiment, the second surface temperature associated with the region of the person may be transmitted to another computing device or displayed using an electronic display.

In some embodiments, the second surface temperature may be used to estimate or compute an internal core temperature for the person. A temperature offset may be determined from a lookup table based on a location of the region of the person and applied to the second surface temperature to compute the internal core temperature for the person. The second surface temperature associated with the region of the person may be determined by averaging temperature values for all pixels covering the region or by averaging the three highest temperature values for pixels covering the region of the person. The region may comprise an inner canthus region or an eye tear duct region of the person.

In some embodiments, it may be detected that a first surface temperature associated with a first region of the person has exceeded a first temperature threshold and then after positioning the person within a second field of view of a second imaging device, it may be detected that a second surface temperature associated with a second region of the person different from the first region of the person has exceeded a second temperature threshold. The regions of the person to which surface temperatures are determined before and after the second imaging device has been repositioned or reoriented may comprise the same region of the person or different regions of the person.

In some embodiments, upon detecting that a first surface temperature exceeds a first temperature threshold, the orientation of the imaging device and the optics of the imaging device may be adjusted such that the person is positioned within a field of view of the imaging device. The field of view may allow for a higher resolution of a target region of the person and/or for higher confidence scores for temperatures associated with the target region of the person. As a person walks within the field of view of the imaging device, the person walks closer to the imaging device, the relative speed of the person may slow down allowing for higher confidence scores for temperatures associated with the target region of the person.

In some examples, a system for screening persons for elevated temperatures comprises an imaging device configured to detect imagery and generate corresponding imagery data of a first target scene and a second target scene. The imagery data can include infrared image data of the first target scene and the second target scene. The system can also include one or more processors in communication with the imaging device. The one or more processors can be configured to receive the imagery data from the imaging device with the infrared image data of the imagery data being indicative of temperatures in the first target scene. The one or more processors can also be configured to identify persons in the first target scene using a portion of the imagery data and determine a temperature of each person identified in the first target scene based at least on the infrared image data. Additionally, the one or more processors can be configured to compare the temperature of each person identified to a first threshold. If the determined temperature of at least one person exceeds the first threshold, the one or more processors can be configured to provide an indication that the at least one person should be directed to the second target scene. The one or more processors can also be configured to receive the infrared image data of the second target scene from the second imaging device with the infrared image data being indicative of a temperature in the second target scene. The one or more processors can further be configured to determine a temperature of the at least one person in the second scene based at least on the infrared image data and can compare the temperature of the at least one person in the second target scene to a second threshold. Also, the one or more processors can be configured to provide an indication of the temperature of the at least one person in the second target scene relative to the second threshold.

In some embodiments, a system for screening persons for elevated temperatures comprises a first imaging device configured to generate imagery data of a first target scene with the imagery data including infrared image data of the first target scene. The system can also include a second imaging device configured to generate imagery data of a second target scene with the imagery data including infrared image data of the second target scene. The system can further include one or more processors in communication with the first imaging device and the second imaging device. The one or more processors can be configured to receive the imagery data of the first target scene from the first imaging device and identify persons in the first target scene using a portion of the imagery data. The one or more processors can further be configured to compare determine a temperature of each identified person in the first target scene based at least on the infrared image data of the first target scene. Further, the one or more processors can be configured to compare the determined temperature of each identified person to a first threshold, and if the determined temperature of at least one person exceeds the first threshold, the one or more processors can be configured to provide an indication that the at least one person should be directed to the second target scene. The one or more processors can additionally be configured to receive the imagery data of the second target scene from the second imaging device and determine a temperature of the at least one person in the second target scene based at least on the infrared image data of the second target scene. The one or more processors can also be configured to compare the temperature of the at least one person in the second target scene to a second threshold and provide an indication of the temperature of the at least one person in the second target scene relative to the second threshold.

In some embodiments, a method of screening persons for elevated temperatures comprises generating imagery data of a first target scene using an imaging device with the imagery data including infrared image data of the first target scene. The method can also comprise identifying persons in the first target scene using a portion of the imagery data and determining a temperature of each person identified based at least on the infrared image data of the first target scene. The method further includes comparing the determined temperature of each person identified to a first threshold. If the determined temperature of at least one person exceeds the first threshold, the method can include providing an indication that the at least one person should be directed to a second target scene. The method can further include generating infrared image data of the second target scene using the imaging device, the second target scene including the at least one person. The method can also comprise determining a temperature of the at least one person based at least on the infrared image data of the second target scene and comparing the temperature of the at least one person in the second scene to a second threshold. Additionally, the method can comprise providing an indication of the temperature of the at least one subject in the second scene relative to the second threshold.

In some embodiments, a system for screening persons for elevated temperatures comprises a first imaging device configured to generate imagery data of a first target scene with the imagery data including infrared image data of the first target scene. The system can also include a second imaging device configured to generate imagery data of a second target scene with the imagery data including infrared image data of the second target scene. The system can further include one or more processors in communication with the first imaging device and the second imaging device. The one or more processors can be configured to receive the imagery data of the first target scene from the first imaging device and identify persons in the first target scene using a portion of the imagery data. The one or more processors can further be configured to compare determine a temperature of each identified person in the first target scene based at least on the infrared image data of the first target scene. Further, the one or more processors can be configured to compare the determined temperature of each identified person to a first threshold, and if the determined temperature of at least one person exceeds the first threshold, the one or more processors can be configured to identify and capture identifying information of the at least one person from imagery of the first target scene. The one or more processors can further be configured to provide an indication that the at least one person should be directed to the second target scene and receive the infrared image data of the second target scene with the infrared image data being indicative of a temperature in the second target scene. The one or more processors can also be configured to use the identifying information of the at least one person to identify the at least one person in the second target scene. Additionally, the one or more processors can be configured to determine a temperature of the at least one person in the second target scene based at least on the infrared image data of the second target scene and can compare the temperature of the at least one person in the second target scene to a second threshold. The one or more processors can also be configured to provide an indication of the temperature of the at least one person in the second target scene relative to the second threshold.

In some embodiments, a method for screening persons for elevated temperatures comprises receiving imagery data including infrared image data of a first target scene from an imaging device with the infrared image data comprising temperature data of the first target scene. The first target scene can be large enough to include a plurality of persons. The method can also include identifying persons in the first target scene using a portion of the imagery data of the first target scene and determining a temperature of each person identified in the first target scene based at least on the infrared image data of the first target scene. The method can further include assigning a confidence factor to the temperature reading associated with at least one person and updating the confidence factor of the temperature reading associated with the at least one person continuously. The method can also include comparing the confidence factor to a threshold confidence factor for the at least one person and directing the at least one person to a second scene if the confidence factor is below the threshold confidence factor.

In some embodiments, a system for screening persons for elevated temperatures comprises a first imaging device configured to generate imagery data of a first target scene, the imagery data including infrared image data of the first target scene, the first target scene being large enough to include a plurality of persons. The system can also include a second imaging device configured to generate imagery data of a second target scene, the imagery data including infrared image data of the second target scene. The system can additionally include one or more processors in communication with the first imaging device and the second imaging device. The one or more processors can be configured to receive the imagery data with the infrared image data of the imagery data being indicative of temperatures in the first target scene. The one or more processors can also be configured to identify persons in the first target scene using a portion of the imagery data and determine a temperature reading of each person identified in the first target scene based at least on the infrared image data of the first target scene. Further, the one or more processors can be configured to assign a confidence factor to the temperature of each person and compare the confidence factor of the temperature to a threshold confidence factor. If the determined confidence factor is below the threshold confidence factor for at least one person, the one or more processors can be configured to provide an indication that the at least one person should be directed to the second target scene.

At least one embodiment of the disclosed technology comprises an electronic computing device including a storage device (e.g., a semiconductor memory) and one or more processors in communication with the storage device. The storage device configured to store a first set of images corresponding with a first field of view of a first imaging device. The one or more processors in communication with the storage device may be configured to determine a first surface temperature associated with a facial region of a person using the first set of images and a temperature measurement confidence value for the first surface temperature, detect that the first surface temperature exceeds a first temperature threshold and that the temperature measurement confidence value exceeds a confidence value threshold, position the person within a second field of view of a second imaging device in response to detection that the first surface temperature exceeds the first temperature threshold and that the temperature measurement confidence value exceeds the confidence value threshold, determine a second surface temperature associated with the facial region of the person using a second set of images corresponding with the second field of view of the second imaging device while the person is within the second field of view of the second imaging device, and output the second surface temperature associated with the facial region of the person.

The disclosed technology may further include one or more processors configured to cause an orientation of the second imaging device to be adjusted such that the person is positioned within the second field of view of the second imaging device. The one or more processors may be configured to determine a distance between the person and the first imaging device and determine the temperature measurement confidence value based on the distance between the person and the first imaging device. In some cases, the one or more processors may be configured to determine a walking speed of the person and determine the temperature measurement confidence value based on the walking speed of the person.

At least one embodiment of the disclosed technology includes determining a first surface temperature associated with a region of a person and a temperature measurement confidence value for the first surface temperature, detecting that the first surface temperature exceeds a first temperature threshold based on the first surface temperature and the temperature measurement confidence value, positioning the person within a second field of view of a second imaging device in response to detecting that the first surface temperature exceeds the first temperature threshold, determining a second surface temperature associated with the region of the person using a second set of images corresponding with the second field of view of the second imaging device while the person is within the second field of view of the second imaging device, and outputting the second surface temperature associated with the region of the person. In some cases, the first field of view may be wider than the second field of view. In some cases, the second imaging device may comprise a higher resolution thermal imaging camera compared with a first imaging device used for determining the first surface temperature.

The disclosed technology may further include determining a distance between the person and a first imaging device and determining the temperature measurement confidence value based on the distance between the person and the first imaging device or determining a walking speed of the person and determining the temperature measurement confidence value based on the walking speed of the person. The disclosed technology may further include positioning the person within the second field of view of the second imaging device by adjusting an orientation of the second imaging device such that the person is positioned within the second field of view of the second imaging device.

At least one embodiment of the disclosed technology includes one or more storage devices containing processor readable code for programming one or more processors to perform a method for improving temperature screening. The processor readable code comprising processor readable code configured to acquire a first set of images of a first target scene from a first imaging device, processor readable code configured to determine a first surface temperature associated with a facial region of a person using the first set of images, processor readable code configured to detect that the first surface temperature exceeds a first temperature threshold, processor readable code configured to position the person within a second target scene in response to detection that the first surface temperature exceeds the first temperature threshold, processor readable code configured to acquire a second set of images of the second target scene from a second imaging device while the person is within the second target scene, processor readable code configured to determine a second surface temperature associated with a portion of the facial region of the person using the second set of images, processor readable code configured to detect that the second surface temperature exceeds a second temperature threshold that is greater than the first temperature threshold, and processor readable code configured to output the second surface temperature in response to detection that the second surface temperature exceeds the second temperature threshold.

The disclosed technology may further include determining processor readable code further comprising processor readable code configured to determine a distance between the person and the second imaging device while the person is within the second target scene, processor readable code configured to determine a walking speed of the person while the person is within the second target scene, and processor readable code configured to detect that the distance between the person and the second imaging device is less than a threshold distance and that the walking speed of the person is less than a threshold speed. In some cases, determining the second surface temperature associated with the portion of the facial region of the person may be performed in response to detection that the distance between the person and the second imaging device is less than the threshold distance and that the walking speed of the person is less than the threshold speed.

At least one embodiment of the disclosed technology includes one or more storage devices containing processor readable code for configuring one or more processors to perform a method for improving temperature screening, wherein the processor readable code configures the one or more processors to: acquire a first set of images of a first target scene from a first imaging device; using the first set of images, determine a first surface temperature associated with a facial region of a person; detect that the first surface temperature exceeds a first temperature threshold; position the person within a second target scene in response to detection that the first surface temperature exceeds the first temperature threshold; acquire a second set of images of the second target scene from a second imaging device while the person is within the second target scene; using the second set of images, determine a second surface temperature associated with a portion of the facial region of the person; detect that the second surface temperature exceeds a second temperature threshold that is greater than the first temperature threshold; and output the second surface temperature in response to detection that the second surface temperature exceeds the second temperature threshold.

The processor readable code may further configure the one or more processors to: determine a distance between the person and the second imaging device while the person is within the second target scene; determine a walking speed of the person while the person is within the second target scene; and detect that the distance between the person and the second imaging device is less than a threshold distance and that the walking speed of the person is less than a threshold speed, wherein the determining the second surface temperature associated with the portion of the facial region of the person is performed in response to detection that the distance between the person and the second imaging device is less than the threshold distance and that the walking speed of the person is less than the threshold speed.

The processor readable code may further configure the one or more processors to: determine an ambient temperature and a time of day; determine a core body temperature for the person based on the second surface temperature, the ambient temperature, and the time of day; and output the core body temperature for the person.

The disclosed technology may be described in the context of computer-executable instructions being executed by a computer or processor. The computer-executable instructions may correspond with portions of computer program code, routines, programs, objects, software components, data structures, or other types of computer-related structures that may be used to perform processes using a computer. Computer program code used for implementing various operations or aspects of the disclosed technology may be developed using one or more programming languages, including an object oriented programming language such as Java or C++, a function programming language such as Lisp, a procedural programming language such as the "C" programming language or Visual Basic, or a dynamic programming language such as Python or JavaScript. In some cases, computer program code or machine-level instructions derived from the computer program code may execute entirely on an end user's computer, partly on an end user's computer, partly on an end user's computer and partly on a remote computer, or entirely on a remote computer or server.

The flowcharts and block diagrams in the figures provide illustrations of the architecture, functionality, and operation of possible implementations of systems, methods, and computer program products according to various aspects of the disclosed technology. In this regard, each block in a flowchart may correspond with a program module or portion of computer program code, which may comprise one or more computer-executable instructions for implementing the specified functionality. In some implementations, the functionality noted within a block may occur out of the order noted in the figures. For example, two blocks shown in succession may, in fact, be executed substantially concurrently, or the blocks may sometimes be executed in the reverse order, depending upon the functionality involved. In some implementations, the functionality noted within a block may be implemented using hardware, software, or a combination of hardware and software.

For purposes of this document, it should be noted that the dimensions of the various features depicted in the figures may not necessarily be drawn to scale.

For purposes of this document, reference in the specification to "an embodiment," "one embodiment," "some embodiments," or "another embodiment" may be used to describe different embodiments and do not necessarily refer to the same embodiment.

For purposes of this document, a connection may be a direct connection or an indirect connection (e.g., via another part). In some cases, when an element is referred to as being connected or coupled to another element, the element may be directly connected to the other element or indirectly connected to the other element via intervening elements. When an element is referred to as being directly connected to another element, then there are no intervening elements between the element and the other element.

For purposes of this document, the term "based on" may be read as "based at least in part on."

For purposes of this document, without additional context, use of numerical terms such as a "first" object, a "second" object, and a "third" object may not imply an ordering of objects, but may instead be used for identification purposes to identify different objects.

For purposes of this document, the term "set" of objects may refer to a "set" of one or more of the objects.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
a set of imaging devices including a first imaging device configured to capture images in a first field of view and a second imaging device configured to capture images in a second field of view;
a storage device configured to store a first set of images corresponding with the first field of view of the first imaging device; and
one or more processors in communication with the storage device configured to:
detect that a region of a person has an exposed surface using the first set of images;
determine a first surface temperature associated with the region of the person using the first set of images and a temperature measurement confidence value for the first surface temperature;
detect that the first surface temperature exceeds a first temperature threshold and that the temperature measurement confidence value exceeds a confidence value threshold;
position the person within the second field of view of the second imaging device in response to detection that the first surface temperature exceeds the first temperature threshold and that the temperature measurement confidence value exceeds the confidence value threshold;
determine a second surface temperature associated with the region of the person using a second set of images corresponding with the second field of view of the second imaging device while the person is within the second field of view of the second imaging device, wherein the second set of images corresponding with the second field of view of the second imaging device covers the region of the person with a greater number of pixels than the first set of images; and
output the second surface temperature associated with the region of the person.

2. The system of claim 1, wherein:
the one or more processors are configured to cause an orientation of the second imaging device to be adjusted such that the person is positioned within the second field of view of the second imaging device.

3. The system of claim 1, wherein:
the one or more processors are configured to determine a distance between the person and the first imaging device and determine the temperature measurement confidence value based on the distance between the person and the first imaging device.

4. The system of claim 1, wherein:
the one or more processors are configured to determine a walking speed of the person and determine the temperature measurement confidence value based on the walking speed of the person.

5. The system of claim 1, wherein:
the first field of view is wider than the second field of view;
the region of the person comprises at least one of an orbital region or a temporal region of a face of the person; and
the first set of images includes one or more infrared images.

6. A method for temperature screening, comprising:
detecting that a region of a person has an exposed surface using a first set of images corresponding with a first field of view of a first imaging device;
determining a first surface temperature associated with the region of the person and a temperature measurement confidence value for the first surface temperature;
detecting that the first surface temperature exceeds a first temperature threshold based on the first surface temperature and the temperature measurement confidence value;
positioning the person within a second field of view of an imaging device different from the first imaging device in response to detecting that the first surface temperature exceeds the first temperature threshold;
determining a second surface temperature associated with the region of the person using images corresponding with the second field of view of the imaging device, wherein the images corresponding with the second field of view of the imaging device cover the region of the person with a greater number of pixels than the first set of images; and
outputting the second surface temperature associated with the region of the person.

7. The method of claim 6, wherein:
the determining the temperature measurement confidence value for the first surface temperature includes determining a distance between the person and the first imaging device and determining the temperature measurement confidence value based on the distance between the person and the first imaging device.

8. The method of claim 6, wherein:
the determining the temperature measurement confidence value for the first surface temperature includes determining a walking speed of the person and determining the temperature measurement confidence value based on the walking speed of the person.

9. The method of claim 6, wherein:
the positioning the person within the second field of view of the imaging device includes adjusting an orientation of the imaging device such that the person is positioned within the second field of view.

10. The method of claim 6, wherein:
the positioning the person within the second field of view of the imaging device includes displaying an indication that directs the person into the second field of view of the imaging device.

11. The method of claim 6, wherein:
the determining the temperature measurement confidence value for the first surface temperature includes detecting a facial obstruction covering at least a portion of the region of the person and reducing the temperature measurement confidence value in response to detecting the facial obstruction.

12. The method of claim 6, further comprising:
determining an internal core temperature for the person based on the second surface temperature; and
outputting the internal core temperature for the person.

13. The method of claim 6, further comprising:
determining an ambient temperature and a time of day;
determining a core body temperature for the person based on the second surface temperature, the ambient temperature, and the time of day; and
outputting the core body temperature for the person.

14. The method of claim 6, wherein:
the determining the first surface temperature associated with the region of the person includes determining a plurality of temperatures associated with a temporal region of the person over a first time period, determining a rate of change for the plurality of temperatures, and extrapolating the first surface temperature associated with the region of the person based on the rate of change for the plurality of temperatures.

15. The method of claim 6, wherein:
the outputting the second surface temperature includes displaying the second surface temperature associated with the region of the person; and
the images corresponding with the second field of view includes one or more infrared images and a resolution of the images is higher than a first resolution of images used to determine the first surface temperature.

16. One or more non-transitory storage devices containing processor readable code for configuring one or more processors to perform a method for improving temperature screening, wherein the processor readable code configures the one or more processors to:
detect that a region of a person has an exposed surface using a first set of images corresponding with a first field of view of a first imaging device;
determine a first surface temperature associated with the region of the person and a temperature measurement confidence value for the first surface temperature;
detect that the first surface temperature exceeds a first temperature threshold based on the first surface temperature and the temperature measurement confidence value;
position the person within a second field of view of a second imaging device different from the first imaging device in response to detection that the first surface temperature exceeds the first temperature threshold;
determine a second surface temperature associated with the region of the person using images corresponding with the second field of view of the second imaging device, wherein the images corresponding with the second field of view of the second imaging device cover the region of the person with a greater number of pixels than the first set of images; and
cause the second surface temperature associated with the region of the person to be displayed.

17. The one or more non-transitory storage devices of claim 16, wherein the processor readable code further configures the one or more processors to:
determine a distance between the person and the first imaging device and determine the temperature measurement confidence value based on the distance between the person and the first imaging device.

18. The one or more non-transitory storage devices of claim 16, wherein the processor readable code further configures the one or more processors to:
determine a walking speed of the person and determine the temperature measurement confidence value based on the walking speed of the person.

19. The one or more non-transitory storage devices of claim 16, wherein the processor readable code further configures the one or more processors to:
adjust an orientation of the second imaging device such that the person is positioned within the second field of view.

20. The one or more non-transitory storage devices of claim 16, wherein the processor readable code further configures the one or more processors to:
determine an internal core temperature for the person based on the second surface temperature and cause the internal core temperature for the person to be displayed.

* * * * *